United States Patent
Hessam

(10) Patent No.: US 12,128,207 B2
(45) Date of Patent: Oct. 29, 2024

(54) ASSEMBLY AND A SYSTEM SUITABLE FOR DISPENSING A LIQUID FROM A COMPRESSIBLE BAG

(71) Applicant: OSAA INNOVATION APS, Hillerød (DK)

(72) Inventor: Ahmed Abdullah Hessam, Hillerød (DK)

(*) Notice: Subject to any disclaimer, the term of this patent is extended or adjusted under 35 U.S.C. 154(b) by 0 days.

(21) Appl. No.: 18/582,830

(22) Filed: Feb. 21, 2024

(65) Prior Publication Data

US 2024/0189570 A1     Jun. 13, 2024

Related U.S. Application Data

(63) Continuation of application No. 17/997,031, filed as application No. PCT/DK2021/050134 on Apr. 29, 2021.

(30) Foreign Application Priority Data

Apr. 30, 2020    (DK) .......................... PA 2020 70274

(51) Int. Cl.
    *A61M 39/28*      (2006.01)
    *A61M 5/168*      (2006.01)

(52) U.S. Cl.
    CPC .......... *A61M 39/28* (2013.01); *A61M 5/16881* (2013.01)

(58) Field of Classification Search
    CPC ........................ A61M 39/28; A61M 5/16881
See application file for complete search history.

(56) References Cited

U.S. PATENT DOCUMENTS 1,556,437 A * 10/1925 Granger ................. B65D 35/28
                                                                                                   222/101
1,660,035 A     2/1928   Fitch
(Continued)

FOREIGN PATENT DOCUMENTS

FR       2 887 458 A1    12/2006
GB       2 204 797 A     11/1988
(Continued)

OTHER PUBLICATIONS

International Search Report and Written Opinion issued in corresponding application PCT/DK2021/050134; Mailing date: Jul. 28, 2021.
(Continued)

*Primary Examiner* — Bob Zadeh
(74) *Attorney, Agent, or Firm* — Pearne & Gordon LLP

(57) ABSTRACT

An assembly and a system suitable for dispensing liquid from a compressible bag, such as for IV treatment of a patient. The assembly includes an apparatus and a flexible mat. The apparatus includes a housing with a dispensing end and an opposite rear end, a floor comprising a flat floor surface, a pair of parallel guiding tracks and a roller arrangement including a roller body. The roller arrangement has a first roller arrangement end and a second roller arrangement end respectively engaged with the respective guiding tracks. The mat has a first mat end, which is mounted to or adapted to be mounted to the roller body and the mat is located at least partly on the flat floor between said guiding tracks.

22 Claims, 24 Drawing Sheets

(56) References Cited

U.S. PATENT DOCUMENTS

| | | | |
|---|---|---|---|
| 2,570,755 A * | 10/1951 | Booth | B65D 35/28 |
| | | | 222/96 |
| 2,837,243 A | 6/1958 | Zebnik | |
| 3,151,616 A | 10/1964 | Selfon | |
| 3,647,117 A * | 3/1972 | Hargest | A61M 5/148 |
| | | | 222/100 |
| 3,853,243 A | 12/1974 | Forman | |
| 4,044,764 A | 8/1977 | Szabo et al. | |
| 4,223,809 A | 9/1980 | Martin | |
| 4,331,265 A * | 5/1982 | Warlick | B65D 35/28 |
| | | | 222/101 |
| 4,575,375 A | 3/1986 | Kozam | |
| 4,805,805 A | 2/1989 | Ocheskey | |
| 4,850,971 A * | 7/1989 | Colvin | A61M 5/148 |
| | | | 222/100 |
| 5,211,626 A | 5/1993 | Frank et al. | |
| 5,692,645 A | 12/1997 | Ryu | |
| 6,194,420 B1 | 2/2001 | Lang | |
| 6,196,420 B1 * | 3/2001 | Gutierrez | B67D 1/0001 |
| | | | 222/101 |
| 6,669,668 B1 * | 12/2003 | Kleeman | A61M 5/148 |
| | | | 222/401 |
| 6,726,655 B1 | 4/2004 | Lieberman et al. | |
| 6,968,977 B1 | 11/2005 | Beene | |
| 8,550,301 B2 | 10/2013 | Szymanski | |
| D847,209 S | 4/2019 | Hessam | |
| 10,604,397 B2 | 3/2020 | Bernede et al. | |
| 2002/0092879 A1 * | 7/2002 | Chrisman | B67D 7/0216 |
| | | | 222/504 |
| 2002/0123741 A1 | 9/2002 | Rake et al. | |
| 2003/0098316 A1 | 5/2003 | Bochno et al. | |
| 2005/0177136 A1 | 8/2005 | Miller | |
| 2008/0149664 A1 | 6/2008 | Schroeder et al. | |
| 2010/0108717 A1 * | 5/2010 | Szymanski | B65D 35/34 |
| | | | 222/100 |
| 2010/0137808 A1 * | 6/2010 | Wilmot | A61M 5/3202 |
| | | | 604/185 |
| 2010/0137832 A1 | 6/2010 | Matthews | |
| 2011/0024464 A1 | 2/2011 | Jaouen | |
| 2014/0008390 A1 * | 1/2014 | Burke | B67D 7/0216 |
| | | | 222/101 |
| 2017/0119958 A1 | 5/2017 | Hessam | |
| 2024/0189570 A1 | 6/2024 | Hessam | |

FOREIGN PATENT DOCUMENTS

| | | |
|---|---|---|
| JP | 2016158932 A | 9/2016 |
| RU | 2451633 C2 | 5/2012 |
| RU | 2493881 C2 | 9/2013 |
| WO | 01/17892 A2 | 3/2001 |
| WO | 2010068415 A1 | 6/2010 |
| WO | 2016192728 A1 | 12/2016 |
| WO | 2019/080982 A1 | 5/2019 |
| WO | 2019/145004 A1 | 8/2019 |

OTHER PUBLICATIONS

Eurasian Patent Office Examination Report, issued May 23, 2024, 202490138.

International Search Report issued in PCT/DK2018/050271, co-pending U.S. Appl. No. 16/758,587, dated Jan. 3, 2019.

Danish Search Report issued in PA 2017 00605, co-pending U.S. Appl. No. 16/758,587, dated Apr. 4, 2018.

Supplementary European Search Report issued in Application No. EP 18 87 0552.9, related to U.S. Appl. No. 16/758,587, dated Jun. 22, 2021.

Danish Search Report issued in corresponding Application No. PA 2020 70274, dated Nov. 3, 2020.

* cited by examiner

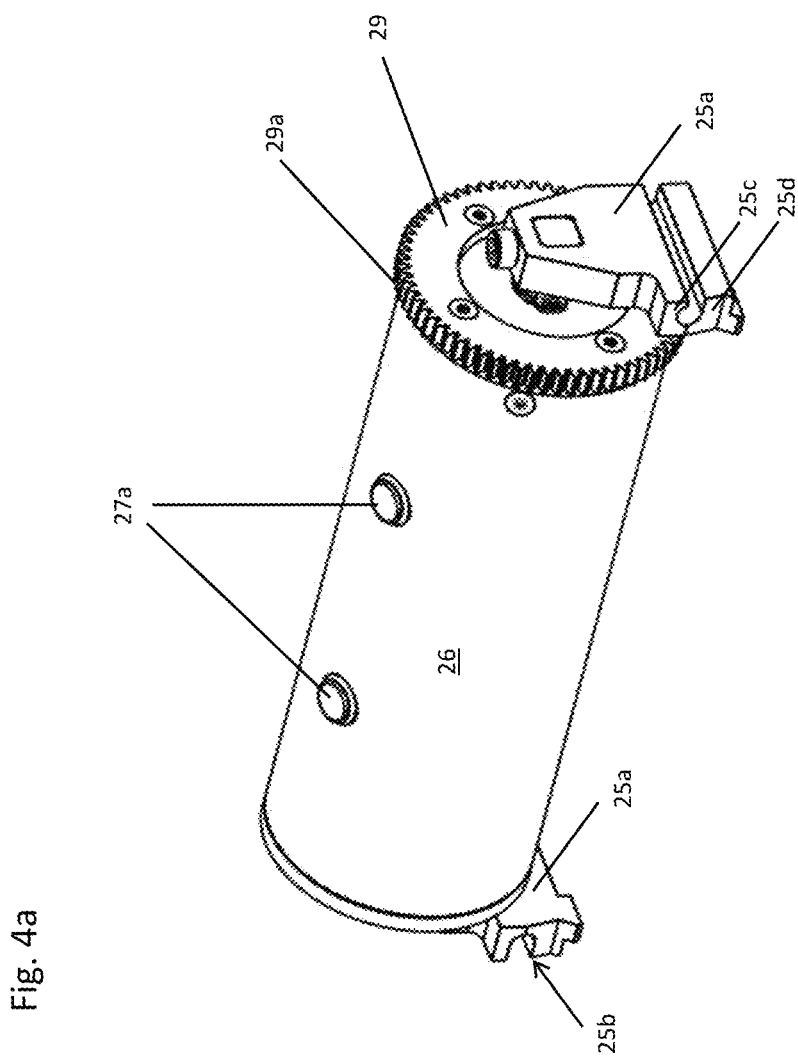

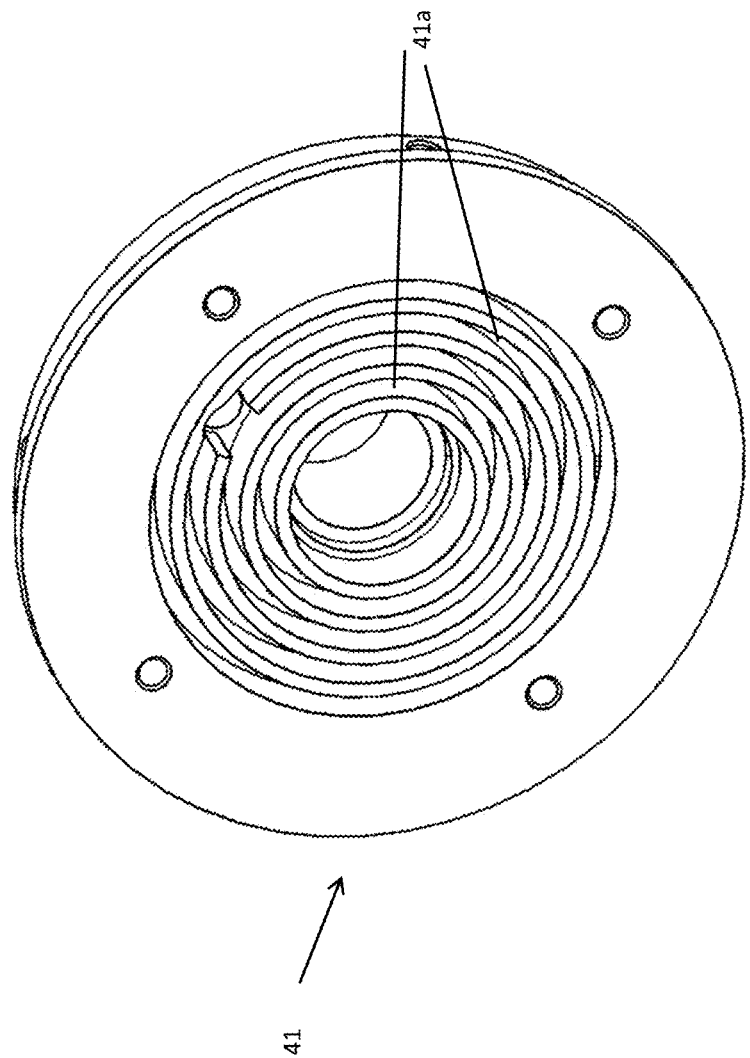

ASSEMBLY AND A SYSTEM SUITABLE FOR DISPENSING A LIQUID FROM A COMPRESSIBLE BAG

CROSS-REFERENCE TO RELATED APPLICATIONS

This application is a Continuation of U.S. application Ser. No. 17/997,031, filed on 2022 Oct. 25, which was a national stage entry of PCT/DK2021/050134, filed on 2021 Apr. 29, that claims the benefit of Denmark Application No. PA 2020 70274, filed 2020 Apr. 30, the entire disclosures of which are hereby incorporated herein by reference.

TECHNICAL FIELD

The present invention relates to an assembly and a system suitable for dispensing a liquid from a compressible bag for example for infusion of liquid or medication in accordance with a predetermined medical therapy.

BACKGROUND

Patients are often, during hospitalization, getting IV treatment in which they receive liquid and medicine into a vein. It is necessary to elevate the IV bag with liquid and medicine, so the liquid can flow into the vein. For IV treatments such as these IV poles are the most commonly used tools.

IV treatments and IV poles greatly influences both patients and the healthcare staffs everyday life in hospitals.

The disadvantage with the IV pole occurs for example when nurses and paramedics have to mobilize patients. It often happens that the hospital staff has to allocate additional resources to mobilize patients.

Furthermore the IV poles occupies a lot of space in the wards and causes the staff poor working conditions due to the fact that they are either in unpleasant working positions or have to adjust the IV poles height to cause the liquid to run faster.

Patients who are dependent of an IV pole may also increase problems with coordination among interdisciplinary staff such as nurses, occupational therapists and physiotherapists at the hospitals. Waiting time can occur, if for example a patient must rehabilitate and at the same time complete an IV treatment.

Another frequent issue hospitals have, is that there is lack of IV poles with wheels. This means that patients are limited in their activities and will therefore need to remain in bed because of their dependence of the IV pole. It is therefore not unusual, that patients are kept unnecessary long time in bed, which again can lead to unnecessary immobilization and increase the risk of bedsores.

Furthermore, IV poles reduce opportunities for children to participate in games and other activities due to dependence of IV poles.

Initiation of births frequently takes place while a pregnant woman is given IV treatment. In this situation, mobilization of the pregnant would be an absolute advantage, because she then would be able to move around freely until the birth has really started.

In acute accidents or treatment of patients outside hospitals and ambulance, it is often required that a person acts as an IV pole.

There have been many attempts to provide a bag pump, which does not require a pole.

U.S. Pat. No. 4,850,971 describes an infusion pump utilizing a linear roller driven by a one or more constant force springs in combination with changeable flow regulating needles to provide a constant flow, gravity independent device. The constant spring springs comprises a coil type that is mounted to a storage drum and an end of the coil springs are attached to a plate such that when the drum is pulled away from the plate the spring is unrolled. In use, the bag is rolled onto the drum between windings of the coil spring.

U.S. Pat. No. 6,669,668 discloses a medication delivery pump that is configured to administer an infusion therapy using a medication delivery container. Medications contained in a flexible bag are expelled from the bag by being and delivered to an infusion site. The fluid delivery pump may have a constant force spring and a mechanical timer, which may limit the maximum rate at which the spring compresses the fluid container. The constant force spring is configured to compress a flexible fluid container. The fluid container in applied onto the unfolded and loaded spring and is compressed between layers of the spring as it rolls up. The mechanical timer assembly is coupled to the constant force spring and limits.

It has been found that during the dispensing of liquid from a bag some curling and shrinkage of the bag frequently appears. The curling and shrinkage of the bag may cause that it is not possible to achieve a satisfactory and reliable emptying of the bag.

DISCLOSURE OF THE INVENTION

An object of the present invention is to provide an assembly and a system suitable for dispensing a liquid from a compressible bag in which the risk of curling and shrinkage of the bag during dispensing is reduced.

In an embodiment, it is an object of the present invention is to provide an assembly and a system suitable for dispensing a liquid from a compressible bag with high reliability and control of the amount and rate of liquid dispensed.

In an embodiment, it is an object to provide an assembly and a system suitable for dispensing a liquid from a compressible bag in which the compressible bag may be emptied to a preselected stage, such as fully emptied.

In an embodiment, it is an object to provide an assembly and a system suitable for dispensing a liquid from compressible bags of different sizes.

This and other objects have been solved by the invention or embodiments thereof as defined in the claims or as described herein below.

It has been found that the invention or embodiments thereof have a number of additional advantages, which will be clear to the skilled person from the following description.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

The term "substantially" should herein be taken to mean that ordinary product variances and tolerances are comprised.

Reference made to "some embodiments" or "an embodiment" means that a particular feature, structure, or characteristic described in connection with such embodiment(s) is included in at least one embodiment of the subject matter disclosed. Thus, the appearance of the phrases "in some embodiments" or "in an embodiment" in various places throughout the specification is not necessarily referring to the same embodiment(s). Further, the skilled person will understand that particular features, structures, or characteristics may be combined in any suitable manner within the scope of the invention as defined by the claims.

Throughout the description or claims, the singular encompasses the plural unless otherwise specified or required by the context.

All features of the inventions and embodiments of the invention as described herein including ranges and preferred ranges may be combined in various ways within the scope of the invention, unless there are specific reasons not to combine such features.

The assembly of the invention comprises an apparatus and a flexible mat. The flexible mat is advantageously mounted to the apparatus. The apparatus comprises a housing having a dispensing end and an opposite rear end. The apparatus also comprises a floor comprising a flat floor surface as well as a pair of parallel guiding tracks and a roller arrangement. The roller arrangement comprises a roller body having a first roller body end and a second roller body end and a roller surface with a cross-sectional circumference. The roller arrangement has a first roller arrangement end and a second roller arrangement end. The first and the second roller arrangement ends are respectively engaged with the respective guiding tracks. The guiding tracks are located to guide the roller arrangement to roll the roller arrangement from the rear end location towards the dispensing end.

The mat has a length extending between a first mat end and a second mat end, wherein the first mat end is mounted to or adapted to be mounted to the roller body.

Advantageously, the mat is located at least partly on the flat floor between the guiding tracks when the roller is located at the rear end location.

A "rear end location" means a location where the roller body is closer to the rear end than to the dispensing end.

The inventors of the present invention have found that the assembly of the invention is surprisingly effective for dispensing liquid from a compressible bag. It has been found that the mat both supports the compressible bag and at the same time ensures an effective dispensing with low or no risk of tearing the compressible bag. In addition, the assembly is simple to use and may be used with practically any type and size of compressible bag.

The second mat end is advantageously located closer to the dispensing end than the first mat end, at least when the roller arrangement is located at the rear end location.

The first mat end may be mounted to the roller body by any method or means. The mounting should advantageously be sufficient to ensure that the mat is rolled onto the roller body when the roller body is rotated. The mounting may e.g. be performed by one or more knobs on the roller body and corresponding slits in the mat to fix the first mat end to the roller body, other fastening methods and means may comprise Velcro fastener(s), adhesive, glue and/or fixing the first mat end by squishing mounting means. In an embodiment, it is desired that the mat may be de-mounted so that it may be replaced with a replacement mat when worn after being used many times.

In an embodiment, the mounting of the mat to the roller body is a chemical (Glue), a physical (tape) and/or a mechanical mounting (mounting in a groove and/or a projection on or in the roller body), preferably the mat is releasable mounted.

In an embodiment, the assembly has a single mat, the mat may comprise one, two or even further layers.

In an embodiment, the assembly comprises a set of mats comprising at least two or more identical mats, In an embodiment, the assembly comprises a set of mats comprising at least two different mats, where the mat may be selected according to a specific use, such as one mat for one type of bags and another mat for another type of bags.

The length of the mat is advantageously selected in dependence of the length of the bag it is adapted for, such that the length of the mat is at least about 2 cm longer than the bag, such as from about 5 cm to about 20 cm longer than the compressible bag. In principle, the mat may be even longer, but this is normally not desired.

In an embodiment, the mat has an extension (length), so that when fully unrolled it is reaching from its mounting to the roller to a distance of 5 cm or less to the dispensing end, preferably to a distance of 2 cm or less to the dispensing end, such as to the dispensing end.

The roller circumference and the mat length may be selected in dependence of each other e.g. to provide that the mat has a length of at least 1.5 times the roller circumference, such as from about 2 to about 10 times the roller circumference. This has the effect of ensuring a smooth rolling onto the roller body with a high control of dispensing rate.

In an embodiment, the mat has a width, which is up to a length of the roller body, preferably up to the distance between the respective guiding tracks, such as up to about 90% of the distance between the respective guiding tracks. Preferably, the width is at least about 5 cm, such as from about 8 cm to about 30 cm, such as from about 10 to about 20 cm. In addition, the width may be selected in dependence of the length of the bag it is adapted for. In an embodiment, the width of the mat is sufficient to apply two or more compressible bag in a side d by side relation onto the mat for simultaneously dispensing.

The mat is advantageously flexible and suitable for being rolled onto the roller body. The mat should advantageously be sufficiently strong for the rolling up without risk of tearing due to the tensile force applied.

The mat has a top surface and an opposite bottom surface facing the floor surface when unrolled from the roller body. The top surface and the bottom surface may be equal or different from each other.

Advantageously the bottom surface has a lower roughness than the top surface. A low roughness of the bottom surface has the effect of providing a low friction between the mat and the floor surface, which again ensures a smooth and controlled rolling onto the roller body. Preferably, the bottom surface has a RA roughness of less than about 10 μm, such as of less than 5 μm, such as of 1 μm or less.

The bottom surface of the mat advantageously has a coefficient of static friction (CoSF) of about 0.3 or less, such as about 0.2 or less, such as about 0.1 or less determined according to ASTM D3702-94 (2019).

The low friction bottom surface may be provided by a suitable low friction polymer e.g. a polymeric coating, such as a resin comprising lubricating particles, such as Tungsten Disulfide ($WS_2$) and/or Molybdenum Disulfide ($MoS_2$).

In an embodiment, the bottom surface is provided by a low friction polymer comprising fluoropolymer, such as PTFE (polytetrafluoroethylene), fluoropolymer, PFA (perfluoroalkoxy) and/or FEP (fluorinated ethylene propylene), the bottom surface is optionally in the form of a layer of the low friction polymer or a coating of the low friction polymer.

PTFE having a CoSF of around 0.05 or less is specifically suitable.

The top surface of the mat advantageously has a relative high friction. This has the function of providing a good grip to the compressible bag, thereby dragging the bag to be squished between the roller body and the mat during the on-rolling of the mat onto the roller body.

In an embodiment, the top surface is provided by a high friction polymer comprising an elastomer, such as a rubber, e.g. a silicone rubber, preferably the high friction polymer has a Durometer, Shore A hardness of 90 or less, such as of 80 or less.

The top surface of the mat may have a high roughness, however advantageously not too high roughness to allow excessive amounts of fluid in the compressible bag escape from being dispensed from the bag.

Each of the top surface and the bottom surface of the mat may independently of each other have one or more surface area having uniform surface characteristic, such as uniform roughness, uniform CoSF, uniform anisotropy. In an embodiment, at least one of the top surface and the bottom surface of the mat comprises at least a surface part having an anisotropic surface characteristic.

In an embodiment, at least one of the top surface and the bottom surface of the mat has a single surface characteristic.

In an embodiment, at least one of the top surface and the bottom surface of the mat comprises two or more surface parts having different surface characteristic. The mat may comprise one or more layers.

The mat may advantageously comprise at least two layers which are interfacially bonded or which are interconnected at least at the first mat end and the second mat end. In an embodiment, the two or more layers are bonded to each other in point-wise bonding spots, where the number, strength and distributions of the point-wise bonding spots ensures that the layers are prevented from delamination during ordinary use.

The floor onto which the mat is applied is advantageously relatively hard and smooth to ensure a low friction between the floor and the mat.

In an embodiment, the floor—preferably the floor providing the floor surface—comprises a rigid polymer, preferably selected from acrylic, polycarbonate, polyimide, PEEK (polyetheretherketone), Acetal (polyoxymethylene), polyamide (such as Nylon 6 or 6/6) or any combinations thereof.

In an embodiment, the floor comprises a cell cast acrylic, such as Plexiglas.

In an embodiment, the floor comprises a fiber reinforced polymer, preferably reinforced with fibers selected from glass fibers, carbon fibers, basalt fibers, aramid fibers or any combinations comprising one or more of these.

In an embodiment, the floor is free of fiber reinforcement.

The floor surface may advantageously have a CoSF of about 0.4 or less, such as about 0.3 or less, such as about 0.2 or less determined according to ASTM D3702-94 (2019).

In an embodiment, the floor surface is provided by a coating of a fluoropolymer, such as PTFE.

In an embodiment, the floor surface has a hardness of at least about 75 Shore D, such as at least about 80 Shore D, such as at least about 85 Shore D, such as at least about 90 Shore D, such as at least about 95 Shore D.

The roller arrangement preferably comprises a track engagement arrangement at each of its respective first second ends engaged with the respective guiding tracks. At least one and preferably both of the track engagement arrangement are each engaged with a slider and/or a wheel to guide the roller arrangement along the guiding tracks and thereby to guide the roller body lengthwise between the slides.

In an embodiment, at least one of the track engagement arrangement comprises a wheel adapted to run onto or in the guiding track, it is engaged with.

In an embodiment, at least one of the track engagement arrangements comprises a track slider engaged with the guiding track for sliding along the guiding tracks, preferably both of the track engagement arrangements comprises a track slider engaged with the guiding track for sliding along the guiding tracks. It has been found that when the track engagement arrangements comprises a track slider engaged with the guiding track for sliding along the guiding tracks a very smooth and stable sliding may be obtained and at the same time the slider is very durable compared to a wheel. Hence, in a desired embodiment one or both of the track engagement arrangements is free of a wheel.

In an embodiment, the track engagement arrangements comprises a grab-lock comprising an upper flange located in contact with an upper side of the track and a lower flange located in contact with a lower side of the track thereby locking the track engagement arrangement (s) to the track and allowing it to slide lengthwise along the track(s). The grab-lock advantageously is or form part of the slider.

In an embodiment, the track engagement arrangements are engaged with the respective guiding tracks to hold the roller body at a predefined and/or selectable distance to the flat floor surface when the roller arrangement passes from the rear end towards the dispensing end.

In an embodiment, the track engagement arrangements are engaged with the respective guiding tracks to hold the roller body at a single predefined distance to the flat floor surface when the roller arrangement passes from the rear end towards the dispensing end.

In an embodiment, the track engagement arrangements are engaged with the respective guiding tracks to hold the roller body at a selected distance to the flat floor surface when the roller arrangement passes from the rear end towards the dispensing end. In this embodiment, the track engagement arrangements and/or the respective guiding tracks are adjustable to allow a user to select the distance between the roller body and the flat floor.

Advantageously, the track engagement arrangements and/or the respective guiding tracks are adjustable to two or more predetermined position resulting in respective predetermined distances between the roller body and the flat floor. Thereby the distance between the roller body and the flat floor may be set to be relatively large when adapted for dispensing fluid from a large/thick compressible bag and the distance between the roller body and the flat floor may be set to be relatively small when adapted for dispensing fluid from a small/thin compressible bag.

In an embodiment, track engagement arrangements are engaged with the respective guiding tracks to hold the roller body in a locked, predefined and/or selectable distance to the flat floor surface when the roller arrangement passes from the rear end towards the dispensing end.

It is desired that the distance between the roller and the flat floor should be larger than the thickness of the mat, preferably such that in use the compressible bag will not be subjected to compression when empty. This has the effect of both ensuring an effective dispensing, while simultaneously ensuring the risk of damaging the compressible bag is very low.

Advantageously, the predefined and/or selectable distance to the flat floor surface from about 2 mm to about 3 cm larger than the thickness of the mat, such as from about 5 mm to about 2 cm larger than the thickness of the mat, such as from about 8 mm to about 1 cm larger than the thickness of the mat.

The mat may in principle be as thick as it is practically possible to roll it onto the roller body. In practice, it is however that the mat is not too thick, because this may require the apparatus to be more bulgy. On the other hand, the mat should advantageously be sufficiently thick to ensure a desired tensile strength and to support the compressible bag under rolling up onto the roller body. A preferred mat thickness is from about 0.1 mm to about 1 cm, such as from about 1 mm to about 5 mm.

Advantageously, the mat at its second mat end has a stop arrangement preventing the second end of the mat to be rolled onto the roller body.

The stop arrangement may for example be a rigid stopper element fixed to the mat at its second end. The rigid stopper may for example be fixed such that it is being blocked from being rolled onto the roller body. The rigid stopper fixed to the mat at its second end may for example being blocked by the track engagement arrangements.

In an embodiment, the stop arrangement is adapted for being blocked by the track engagement arrangements when the track engagement arrangements reached the second end of the mat. The rigid stopper may for example comprise rigid rod, such as a rigid rod with a length dimension wherein the rigid rod may be mounted with its length dimension perpendicular to the guiding tracks.

The roller arrangement may have a center axis located in a center axis plane parallel to the flat floor surface, when the roller arrangement passes from the rear end towards the dispensing end.

The center axis plan may comprise the guiding tracks.

The apparatus may comprise a drive arrangement engaged with the roller arrangement for driving the roll of the roller arrangement from the rear end towards the dispensing end. The drive arrangement comprises a spring arrangement and/or an electric motor.

Advantageously the drive arrangement is adapted for driving the roller body in counterclockwise direction when seen from side where the dispensing end is located left to the roller body. Thereby the mat and a compressible bag if located onto the mat will be passed below the roller body and rolled onto the roller body during dispensing.

The drive arrangement preferably comprises a spring arrangement, wherein the spring arrangement comprises a single spring or a multi spring arrangement, such as a spring arrangement comprising two or more springs operating in parallel.

The drive arrangement may for example comprise a spring arrangement fully or partly located in the roller body, i.e. located within the wall surface of the roller body.

Advantageously, the spring arrangement comprises at least one helical torsion spring located within the roller body. The roller body may form a housing for the one or more helical torsion springs.

In an embodiment, the roller arrangement comprises an axle and the roller body is arranged to rotate around the axle driven by the spring arrangement.

In an embodiment, at least one helical torsion spring is located between the roller body and the axle. The axle may be directly or indirectly rigidly connected to at least one axle flange and a first end of the helical torsion spring may be engaged with the roller body and a second end of the helical torsion spring may engaged with the axle flange. Thereby the rotation of the roller body may be driven to rotate around the axle by the spring arrangement when the helical torsion spring is in loaded condition. The axle may be releasable from its engagement with the axle e.g. for adjusting the relation between the axle and the roller body relative to the spring loading stage, i.e. to ensure that the fixation means on the roller body is located in a desired position when the spring(s) is in unloaded condition.

The roller body may comprise a cylindrical body part and at least one roller flange perpendicular to the cylindrical body and/or to the axle. The first end of the helical torsion spring may be engaged with the roller flange and/or with the cylindrical body part.

In an embodiment, at least one of the axle flanges is/are an engagement axle flange and at least one of the roller flanges is/are an engagement roller flange, wherein the engagement axle flange is engaged with the engagement roller flange, preferably to control, steer and/or restrain the rotation of the roller body. The engagement axle flange and the engagement roller flange are advantageously engaged by corresponding annular flanges, annular channels and/or annular sections of flanges.

In a preferred embodiment, the engagement axle flange and the engagement roller flange forms a rotational restraint, restraining the rotation of the roller body to a predefined rotation rate. The restraint has the function of ensuring that a desired driving force is transmitted from the spring arrangement to the roller body, this ensures in addition that the spring arrangement may be loaded to a high degree to ensure a full and essentially constant dispensing of liquid from a compressible bag.

In an embodiment, the engagement axle flange and the engagement roller flange forms a rotational restraint, wherein a first of the engagement axle flange and the engagement roller flange comprises annular channels and a second of the engagement axle flange and the engagement roller flange comprises annular flanges or sections of flanges engaged into the annular channels of the first of the engagement axle flange and the engagement roller flange. The annular channels may advantageously comprises a lubricate, such as an oil or grease. Preferably the lubricate is filling up at least about 75% by volume, such as at least about 85% by volume such as at least about 95% by volume of the space in the channels between the annular flanges or sections of flanges. There by a desired damping of the force transferred from the spring arrangement to the roller body may be ensured.

Preferably, the lubricate can pass from one annular channel to another annular channel, e.g. through perforations in the annular flanges and/or between sections of flanges. This ensures a simple and effective way of adjusting the damping. In an embodiment, the rotational restraint is adjustable by adjusting the size of the flange(s) (e.g. penetration depth into the channel(s)) and/or by adjusting the amount of lubricant in the channel(s).

In an embodiment, the annular channels each has a channel width and wherein at least one of the annular flanges or sections of flanges engaged into an Annular channel has a width of from about 75% to about 100%, such as from about 90% to about 99% of the channel width of the channel.

The spring arrangement may comprise a loading arrangement for at least partly loading the spring arrangement. The loading arrangement is preferably arranged for at least partly loading the spring arrangement by unrolling the mat from the roller body and or by moving the roller arrangement in a direction from the dispensing end and towards the rear end.

Advantageously, the spring arrangement comprises a loading station for loading the spring arrangement. The loading station may advantageously be located to engage with the roller arrangement at rear end location of the housing.

In an embodiment, the loading station comprises a toothed wheel and a bar for rotating the toothed wheel. The roller body may comprise a ring of tooths located to engage with the toothed wheel when the roller body is located in the loading station. Preferably the ring of tooths is located on a periphery of a roller flange located at one of the roller body ends.

For providing a loading station that effective and relatively simple to use, the roller arrangement may advantageously comprise a snap lock for temporarily holding the roller body in the loading station. In addition, it is desired that the roller arrangement comprises a lever for releasing the roller body from the loading station, to ensure that a user may release the roller body from the loading station after desired and/or completed loading of the spring(s) of the spring arrangement.

The apparatus may conveniently comprise a top part, such as a lid, which may be fully or partly moved for allowing access to the mat. The lid ensures that unintentional compression of a compressible bag located in the assembly may be prevented and at the same time, it protects against dust.

Advantageously, a rear section of the housing forms a shelter for the roller arrangement, when located in a rearmost position. The roller body may advantageously be located in the shelter when engaging with the loading station. Thereby the shelter forms an extra protection of the loading station.

The apparatus may advantageously comprise one or more sensors. In an embodiment, the apparatus comprises a monitor sensor and a display for monitoring and displaying least one condition of a compressible bag arranged on the mat. The condition condition(s) may advantageously include a temperature of the liquid in the compressible bag and/or under dispensing from the bag and/or at least one dispensing condition, such as dispensing rate, dispensing status or dispensing time left.

The apparatus may comprise a transmitter for wireless transmission (e.g. using Bluetooth technology) to a user e.g. a handheld tablet of a nurse.

In an embodiment, the apparatus comprises a regulator arrangement for automatic or remote controlling of start or stop of dispensing of liquid from a bag located on the mat.

The monitor sensor may be integrated with or associated to the regulator arrangement.

In an embodiment, the apparatus comprises a display for displaying a loading condition of the spring arrangement.

Advantageously, the apparatus comprises a temperature regulating arrangement adapted to heat a liquid in the compressible bag located on the mat. The temperature regulating arrangement may comprises one or more heating elements incorporated into the mat, into the floor and/or into the lid.

In an embodiment, the temperature regulating arrangement comprises an air heat blower arranged for heating the space within the housing to a selected temperature.

The temperature regulating arrangement may advantageously comprises at least one temperature sensor. The temperature sensor may advantageously be associated with the heating element(s) for controlling the heating element(s).

In an embodiment, the one or more sensors is/are located in the floor, the mat, and/or in the track(s).

The invention also comprises a system suitable for dispensing liquid from a compressible bag. The system of the invention comprises the assembly as claimed and as described above in combination with a compressible bag.

The compressible bag has a rear end and a dispensing end, the dispensing end comprises a dispensing port suitable for being connected to a tubing arrangement for administering the liquid to a patient.

Any suitable tubing arrangement may be applied, such as the type of tubing arrangement used in prior art dispensing system for dispensing liquid from a compressible bag.

In an embodiment of the system, the mat has a width, which is as least a large as a width of the compressible bag.

In an embodiment of the system, the mat has a length, which is as least as long as the distance between the rear end and the dispensing end of the compressible bag.

Advantageously, the track engagement arrangements are engaged with the respective guiding tracks to hold the roller at a predefined and/or selectable distance to the flat floor surface when the roller arrangement passes from the rear end towards the dispensing end as described above, wherein the predefined and/or selectable distance to the flat floor surface is from about 1 mm to about 2.5 cm larger than the combined thickness of the mat and the compressible bag in empty condition, such as from about 2 mm to about 2 cm, such as from about 4 mm to about 1 cm larger than the combined thickness of the mat and the compressible bag in empty condition.

In an embodiment, the system further comprises the tubing arrangement for administering the liquid wherein the tubing arrangement comprises a tube and a roller pinch clamp for adjusting the flow through the tube.

Advantageously, the roller pinch clamp comprises at least two adjustment rollers. The two or more adjustable rollers of the roller pinch clamp ensures a highly accurate velocity adjustment which in addition is relative simple to use Advantageously the at least two adjustment rollers of the roller pinch clamp are located opposite to each other for directly and or indirectly via a support flange pinching the tube between the rollers. Thereby the adjustment may be performed in a very simple way. The tube may e.g. be located in a housing between two flanges and the two rollers are located to compress the tube between the two flanges. In a variation there of the rollers are acting directly on the tube.

In an embodiment, the tubing arrangement comprises a spike and drip chamber connected between the dispensing port and the tube. The roller pinch clamp may preferably be integrated with the drip chamber or be located at a distance to the drip chamber along the tube of up to about 0.5 m, such as up to about 0.2 m, such as up to about 0.1 m.

By having the roller pinch clamp integrated with the drip chamber or located very close to the drip chamber e.g. up to about 5 cm from the drip chamber the combined roller pinch clamp and drip chamber may be adjusted using one hand.

BRIEF DESCRIPTION OF THE EXAMPLES AND DRAWING

The invention is illustrated further below in connection with embodiments and with reference to the figures. The figures are schematic and may not be drawn to scale.

FIG. 3c illustrates a variation of the embodiment shown in FIG. 3a.

FIG. 4a is a schematic and perspective view of a roller arrangement of an assembly of an embodiment of the invention where a first end of the roller arrangement is in focus.

FIG. 4c illustrates a variation of the embodiment shown in FIG. 4a.

FIG. 5b illustrates a variation of the embodiment shown in FIG. 5a.

FIG. 6b illustrates a variation of the embodiment shown in FIG. 6a.

FIG. 7b illustrates a variation of the embodiment shown in FIG. 7a.

FIGS. 8a and 8b are schematic and perspective views of a set of flanges comprising an engagement axle flange and an engagement roller flange forming a rotational restraint.

FIG. 8c illustrates a variation of the embodiment shown in FIG. 8a.

FIG. 8d illustrates another variation of the embodiment shown in FIG. 8a.

Figure 1:
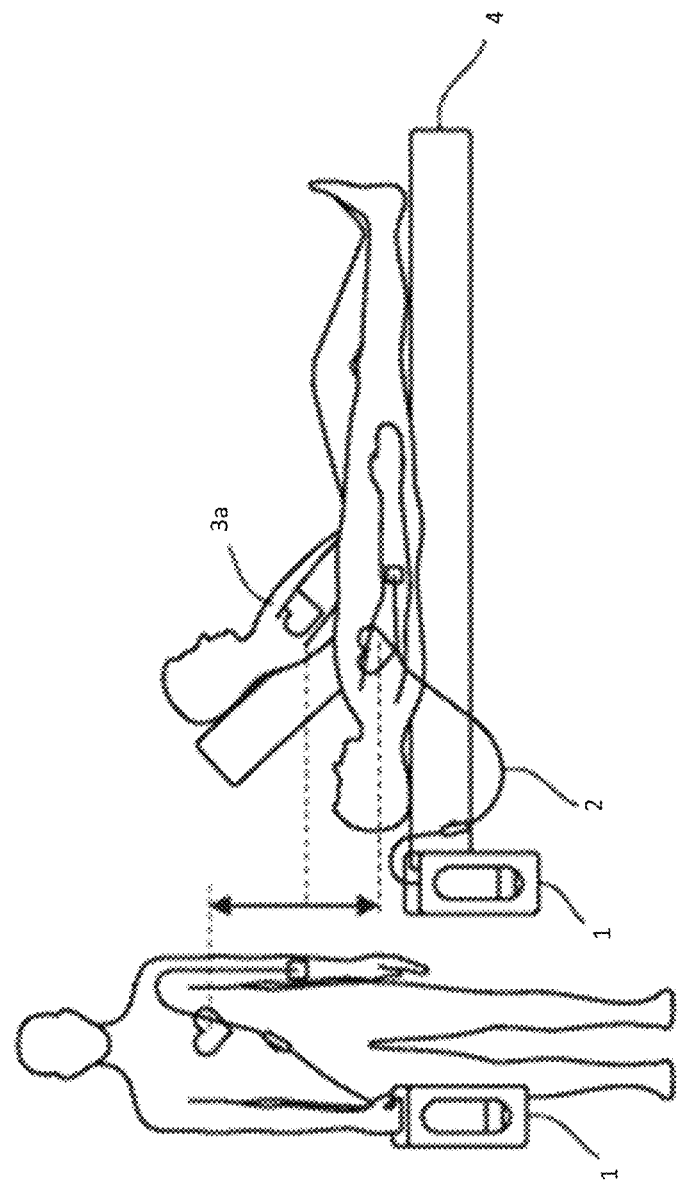
FIG. 1 illustrates a patient using an assembly of an embodiment of the invention.

FIG. 1 shows a patient in different positions using an assembly system comprising an assembly of an apparatus and a mat as described above and a tubing arrangement as described above. In the right side of FIG. 1, the patient 3 is lying in a bed 4. The patient 3 may be lying flat or be sitting in the bed 4. The assembly 1 comprises the apparatus and the not shown mat and with a compressible bag from which a liquid is dispensed via a tubing arrangement 2 to the patient. The assembly 1 is hanging on the side of the bed 4, i.e. lower than the level of the heart 3a of the patient 3. This is possible because the assembly 1 provides a desired, reliable and constant dispensing of the liquid from the bag independently of the level of the assembly 1 relative to the patient's heart 3a. In the left side of the figure, the patient 3 is standing with the assembly 1 in his hand—i.e. far below heart level. The assembly 1 is ensuring a very reliable and steady dispensing rate until the compressible bag is empty. There is no risk of backflow even when the assembly 1 is located at a very low level relative to the heart 3a. At the same time, the assembly 1 is very compact and easy to handle by the patient and nurses. The assembly 1 may be carried by the patient 3 by hand, on his shoulder or bag or be hanged on a wheelchair or a walker and etc. The reliability of the assembly 1 makes the assembly very simple to use and no pole is required.

Figure 2:
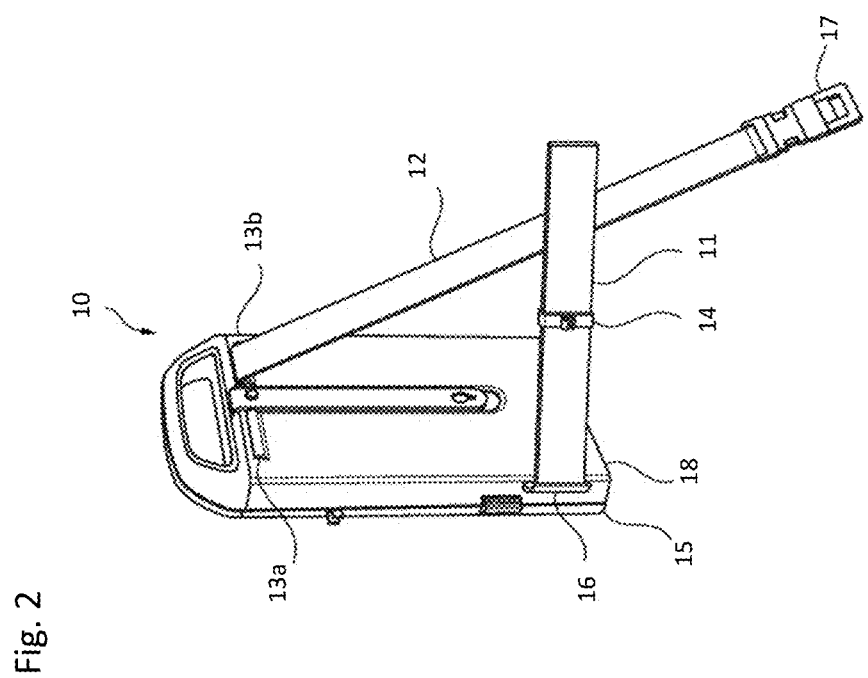
FIG. 2 illustrates an assembly comprising a set of straps e.g. as described in WO2019145004.

In FIG. 2 the assembly 10, comprises a set of straps e.g. as described in WO2019145004. In this embodiment, the set of straps comprises two main straps 11 and 12. A first main strap 11 is attached with one end to a first bottom portion connecting structure 16 located on a first side panel 15 of the assembly 10 adjacent to its dispensing end 18. The other end of the strap 11 may be attached to the first top portion connecting structure 13a of the assembly 1.

A second main strap 12 is attached to a second top portion connecting structure 13b with its first end. The second end of the main strap 12 may be attached to a second bottom portion connecting structure (not visible) on the assembly e.g. using a buckle 17.

Thus, a patient to carry the assembly 1 on the bag can use the main straps 11 and 12. The main strap 11 is mounted with a tube holder 14, which may be used to fix a tube of a tubing arrangement, e.g. during IV treatment. The straps may be connected to the apparatus of the assembly at several positions e.g. as described in WO2019145004.

Figure 3A:
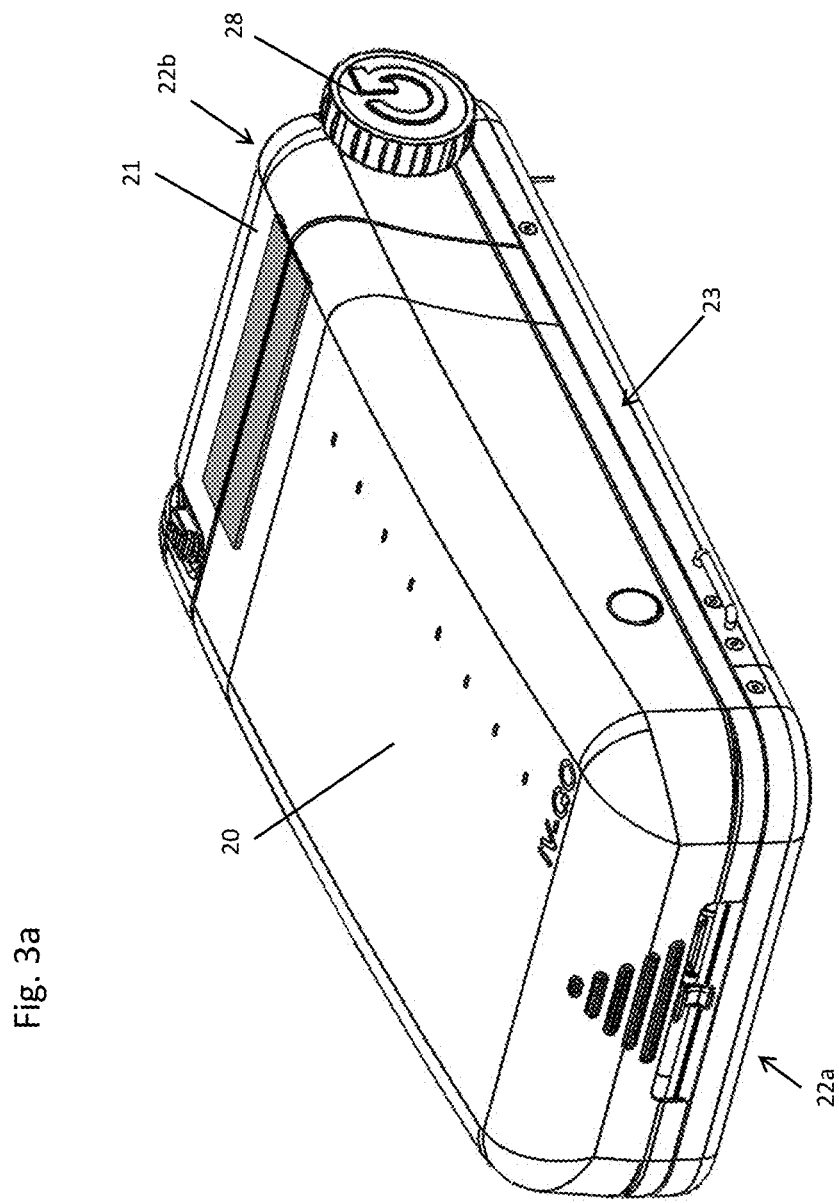
FIGS. 3a and 3b illustrate an assembly of an embodiment of the invention seen in perspective and where the lid is closed.
Figure 3B:
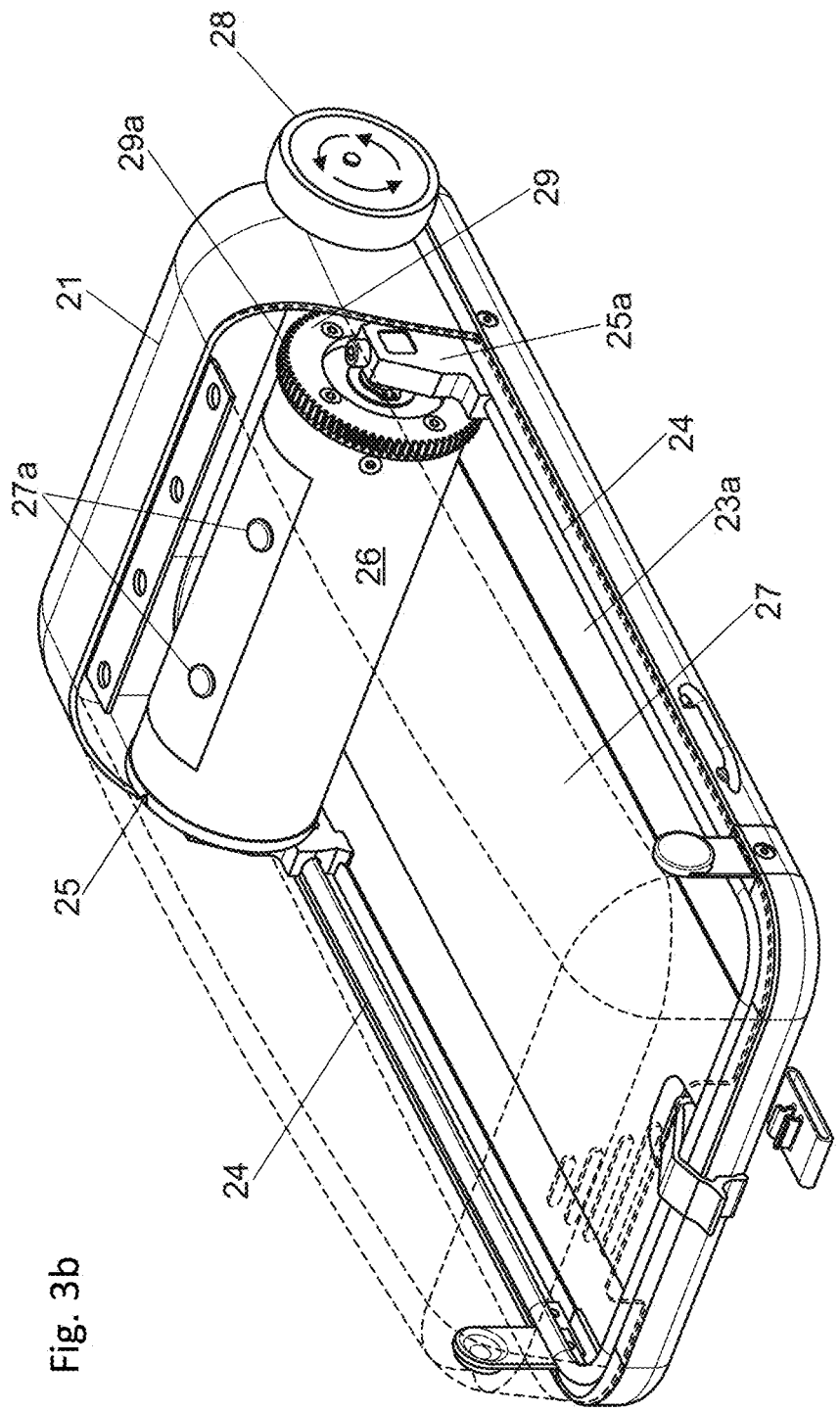
Figure 3C:
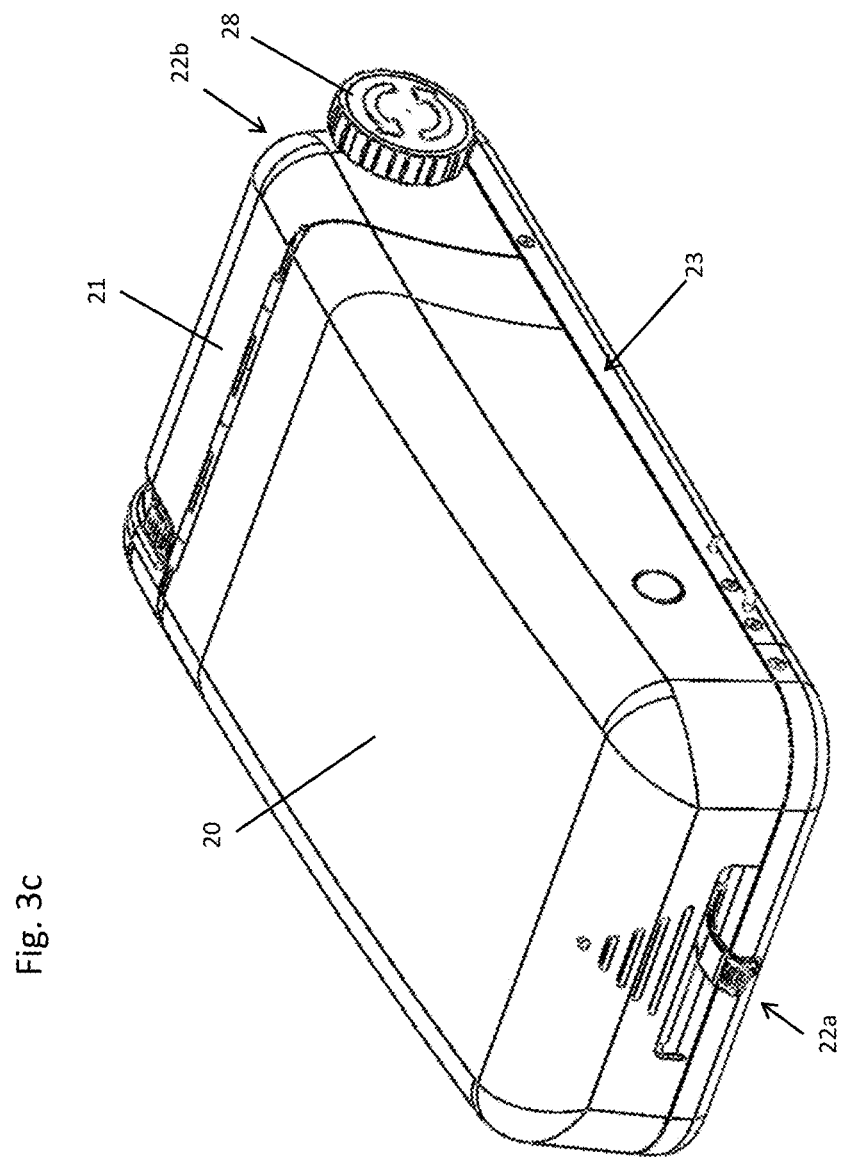

In FIGS. 3a and 3b the assembly is shown in closed condition i.e. with the lid 20 closed. In FIG. 3b, the lid is transparent, whereas more details of the lid may be seen in FIG. 3a. The assembly comprising an apparatus with a housing having a dispensing end 22a and an opposite rear end 22b. A bottom portion 23 forms a floor comprising a flat floor surface onto which a mat 27 is located. A first mat end is fixed to the roller body 26 via a pair of knobs 27a. The apparatus comprises a pair of parallel guiding tracks 24 and a roller arrangement 25 comprising a roller body 26 having a first and a second roller body ends and a roller surface with a cross-sectional circumference.

The roller arrangement comprises a track engagement arrangement at each of its respective first second ends engaged with said respective guiding tracks roller arrangement 25 comprises a track engagement arrangement 25a at each of its respective first second ends engaged with the respective guiding tracks 24. In the FIGS. 3a and 3b only one of the track engagement arrangements 25a as visible.

The apparatus comprises a drive arrangement for driving the roller body 26. The drive arrangement comprises a spring arrangement including a torsion spring located between the roller body 26 and an axle of the roller arrangement 25. The apparatus comprises a loading station for loading the torsion spring. The loading station is located in a rear end of the housing where the housing forms a shelter 21 for the roller body 26 when located in the loading station. The loading station comprises a toothed wheel and a bar 28 for rotating the toothed wheel. The roller body comprises a ring of tooths 29 located on a periphery of a roller flange 29 located a roller body end to engage with the toothed wheel when the roller body is located in the loading station.

Figure 4B:
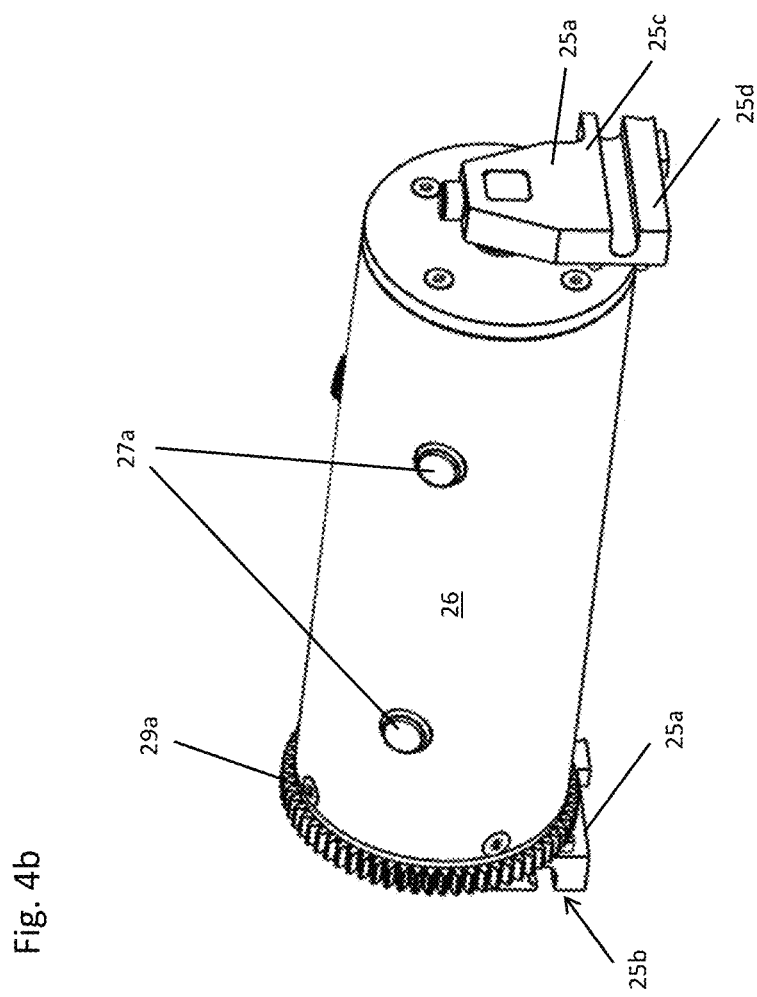
FIG. 4b is another schematic and perspective view of the roller arrangement shown in FIG. 4a where the second end of the roller arrangement is in focus.
Figure 4C:
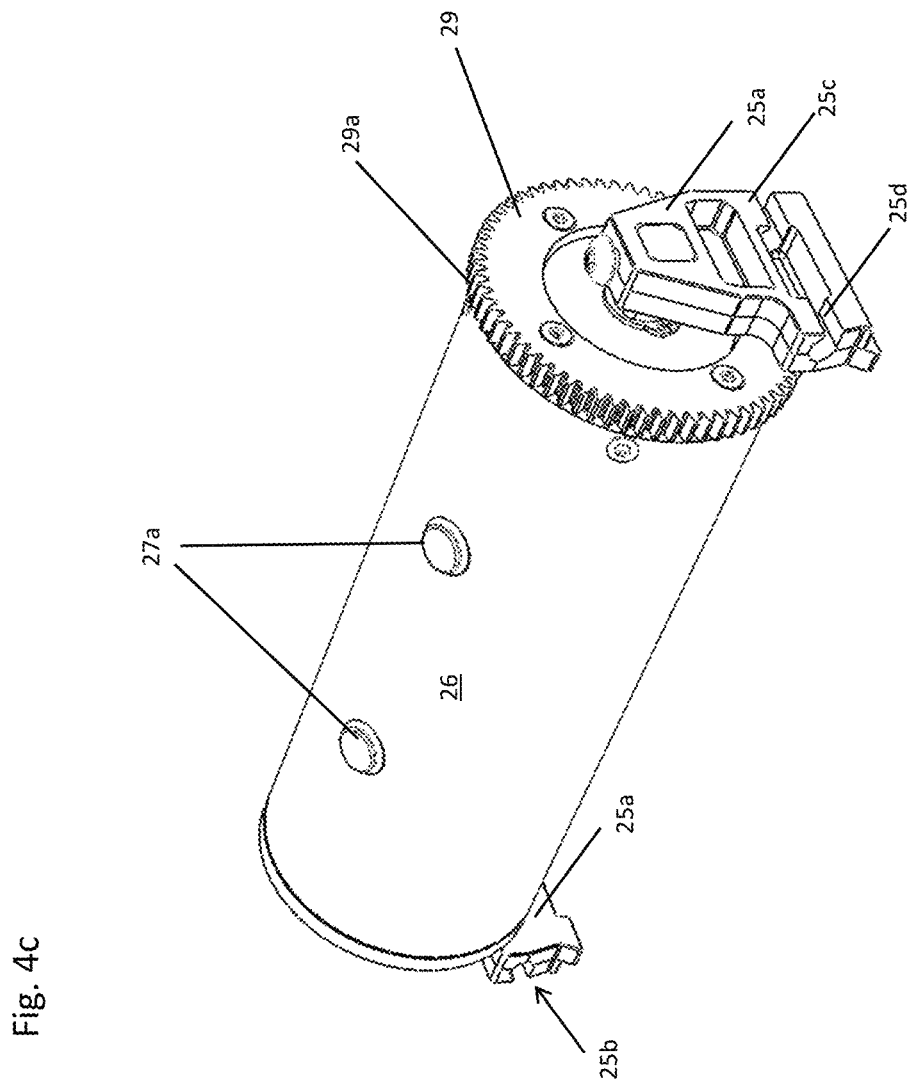
Figure 4D:
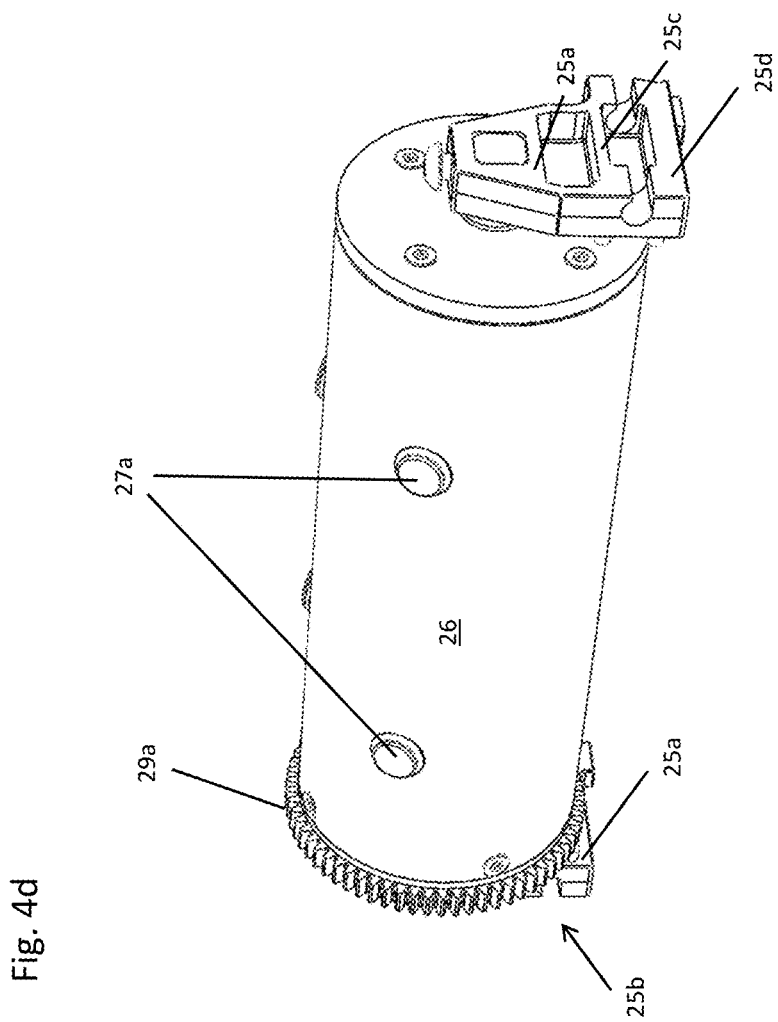
FIG. 4d illustrates a variation of the embodiment shown in FIG. 4b.

FIGS. 4a and 4b show the roller arrangement without the mat, where the first roller arrangement end and the second roller arrangement end can be seen on respectively FIGS. 4a and 4b.

The track engagement arrangements 25a comprises each a track slider 25b engaged with the guiding track 24 for sliding along the guiding tracks 24.

The track slider 25b comprises a grab-lock comprising an upper flange 25c located in contact with an upper side of the track 24 and a lower flange 25c located in contact with an lower side of the track thereby locking the track engagement arrangement (s) to the track and allowing it to slide lengthwise along the track(s). The grab-lock advantageously is or comprise the slider.

Figure 5A:
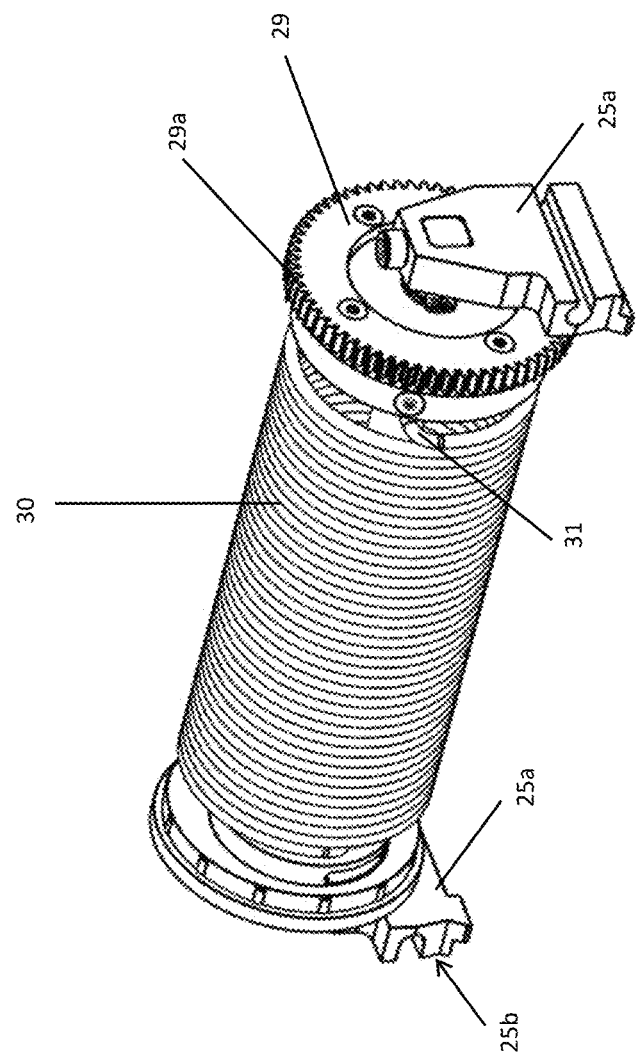
FIG. 5a illustrates the roller arrangement of FIG. 4a, where the cylindrical body part of the roller body has been removed.
Figure 5B:
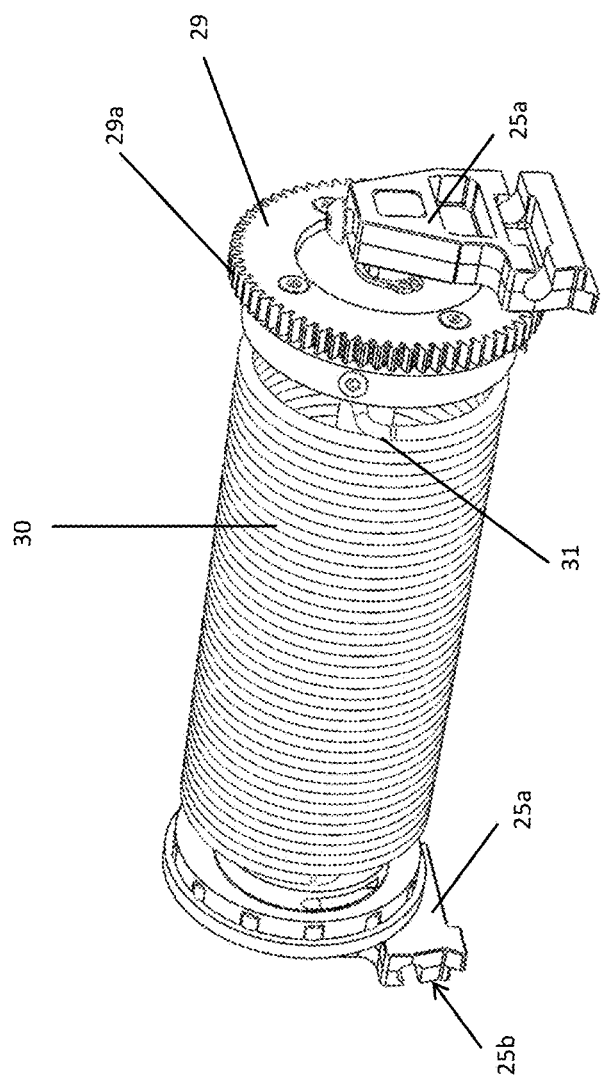

In FIG. 5a, the cylindrical body part of the roller body has been removed and the torsion spring 30 of the drive arrangement is visible. The drive arrangement may comprises two or more torsion springs. A first end of the helical torsion spring 31 is adapted for being engaged with the roller body directly or indirectly e.g. via a flange connected to the roller body.

Figure 6A:
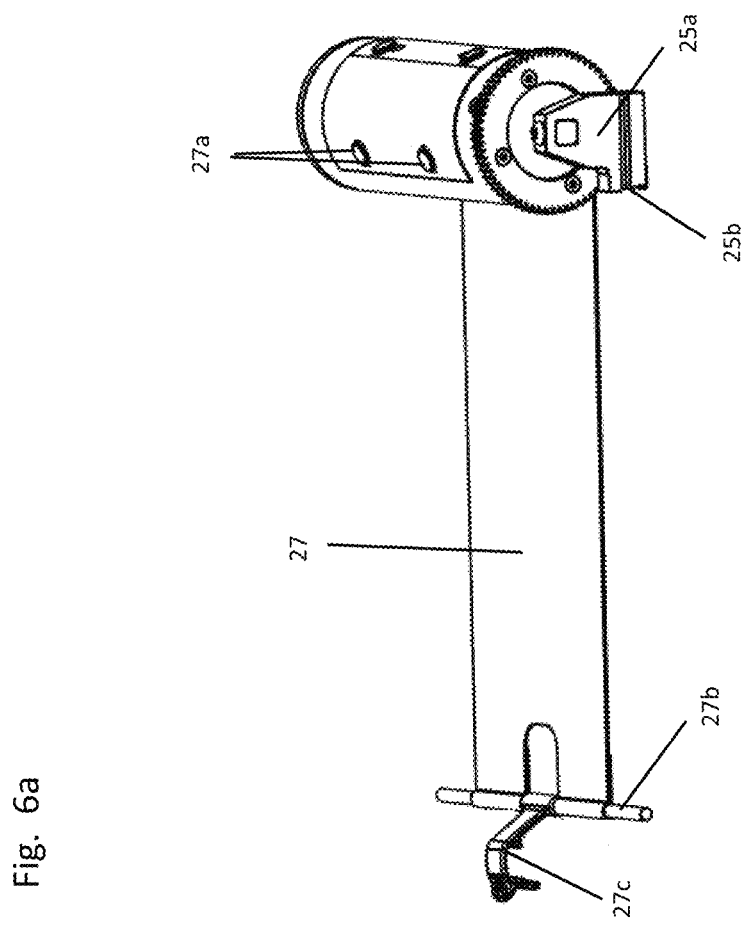
FIG. 6a is a schematic and perspective view of a roller arrangement combined with a mat of an embodiment of the invention.
Figure 6B:
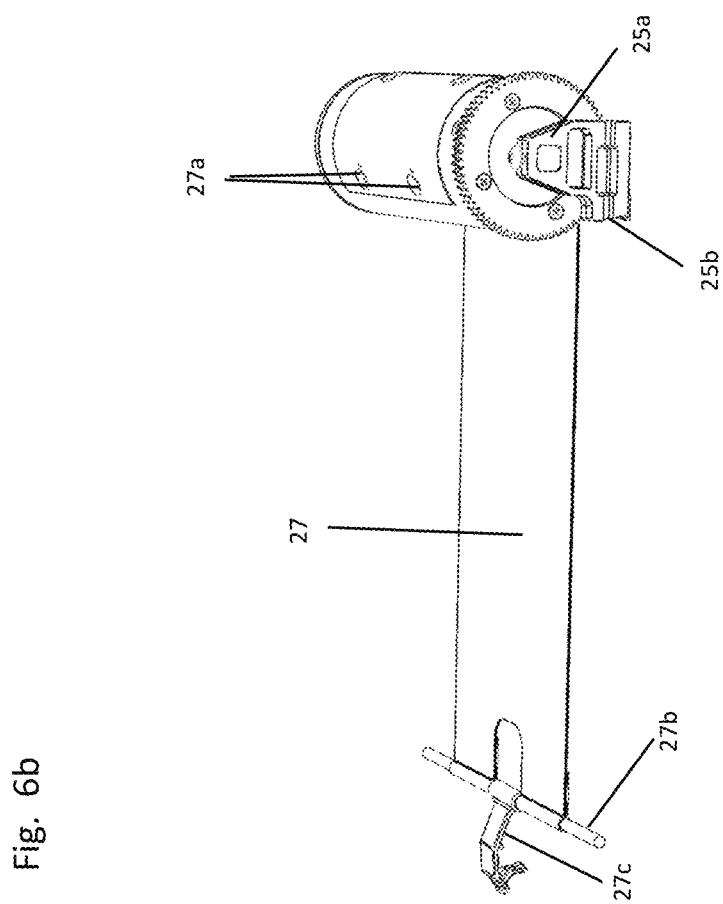

FIG. 6a shows the roller arrangement in combination with the mat 27. The first mat end is fixed to the roller body 26 via a pair of knobs 27a. Thereby when the drive arrangement drives the roller body to rotate a compressible bag located onto the mat 27 will be trapped between the roller body 26 and the mat 27 and the compressible bag will be compressed to dispense the liquid from the compressible bag. At the second end of the mat 27, it comprises a stop arrangement in the form of a rigid rod 27b and a strap 27c for unrolling the mat after a terminated dispensing. The rigid rod 27b ensures that the second end of the mat 27 is not fully rolled onto the roller body, in that the slider 25b blocks the rigid rod 27b. After a terminated dispensing, the mat may be unrolled from the roller body simply by tearing in the strap 27c.

Figure 7A:
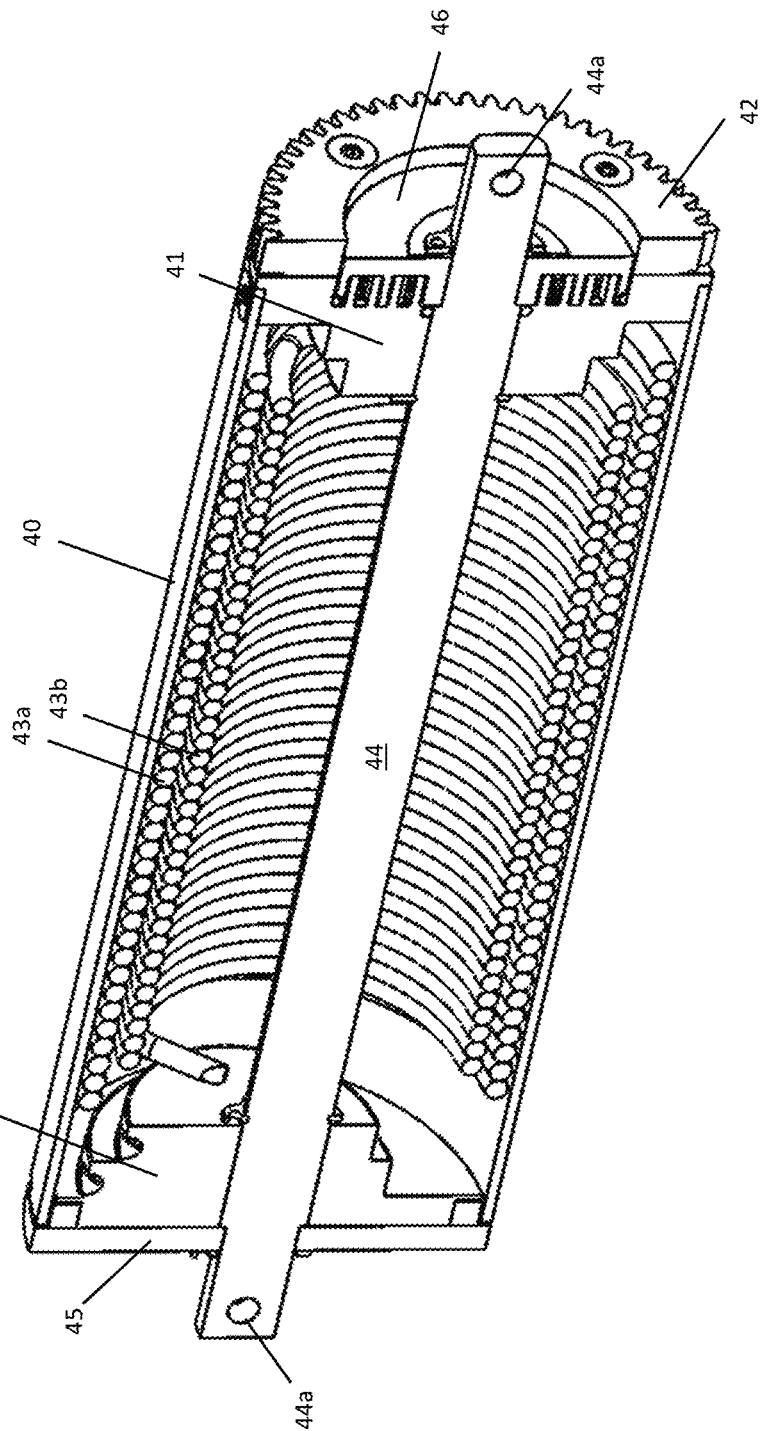
FIG. 7a is a schematic, cross-sectional view of a roller arrangement of an assembly of an embodiment of the invention.

FIG. 7a shows the inside of a part of the roller arrangement. The roller arrangement comprises the roller body, two torsion springs 43a, 43b and an axle 44 with mounting holes 44a at each end thereof and axle flanges. The roller body comprises a cylindrical body part 40, an engagement roller flange 41 and the toothed flange 42 for loading the torsion springs 43a, 43b. The axle 44 is rigid connected to axle flanges 45 and 46 and indirectly rigid connected to axle flange 47. Axle flange 45 is located at an end of the roller body, but the roller body is rotatable relative to the axle flange 45. The axle flange 45 is releasable rigidly connected to the axle flange 47. The axle flange 46 is an engagement axle flange, which together with the engagement roller flange 41 forms a rotational restraint, restraining the rotation of the roller body to a predefined rotation rate.

A first end of each of the springs 43a, 43b is engaged with the roller body, here via the engagement roller flange 41. The second end of each of the springs 43a, 43b is engaged with the axle flange 47, which is rigidly connected to the axle via axle flange 45. The rigidly connection between axle flange 45 and axle flange 47 is releasable so that it may be released for adjusting the relation between the axle and the roller body relative to the spring loading stage, i.e. to ensure that the fixation means on the roller body is located in a desired position when the spring(s) is in unloaded condition. The releasable locking between axle flange 45 and axle flange 47 may be provided by an arrangement of small rollers or other suitable means.

Figure 7B:
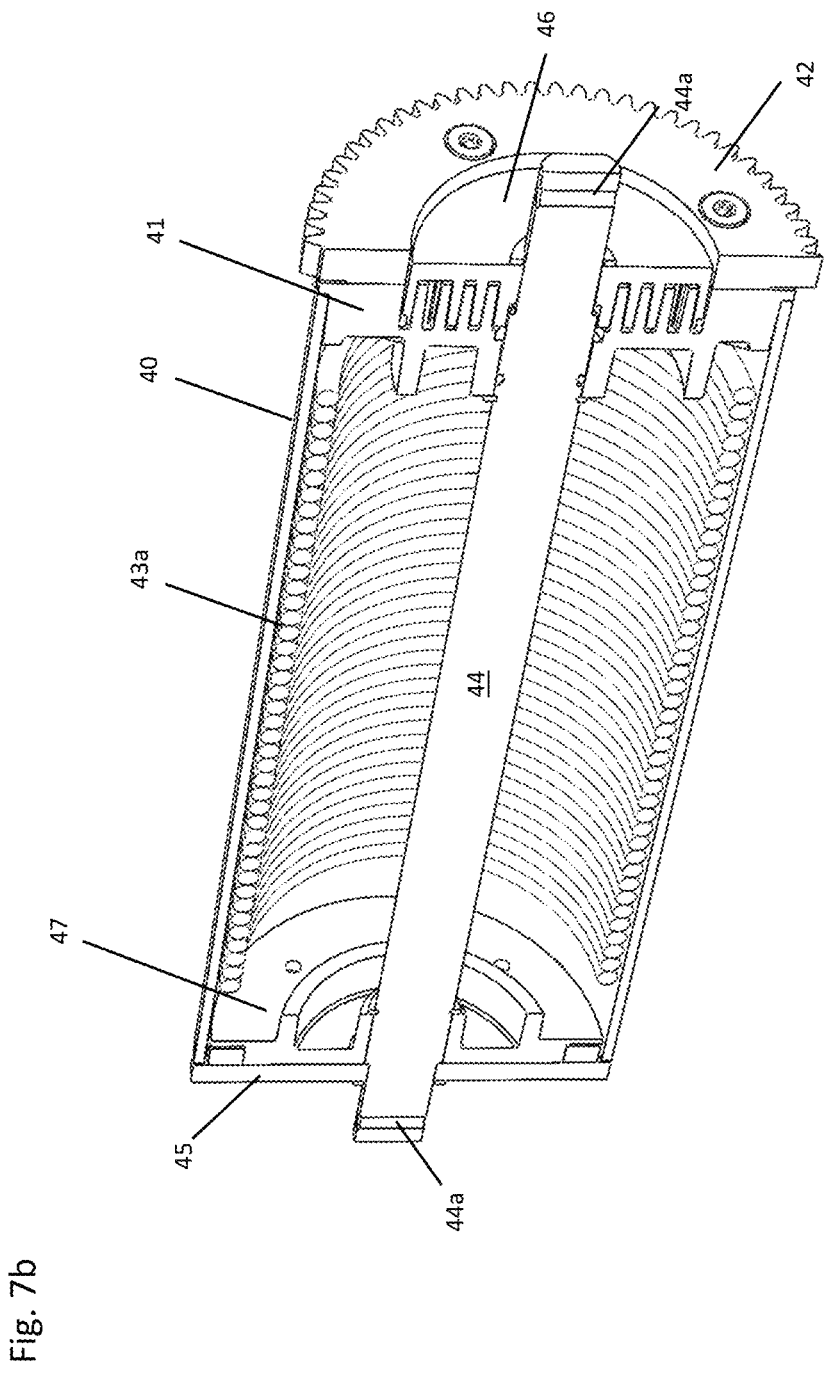
Figure 8A:
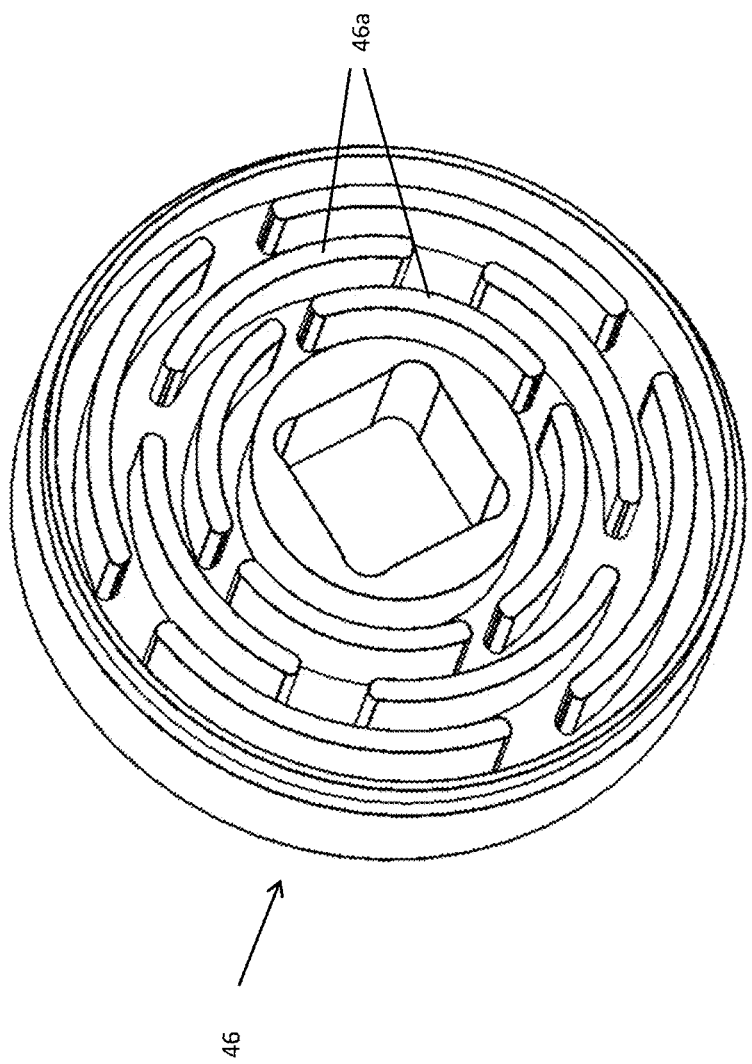
Figure 8C:
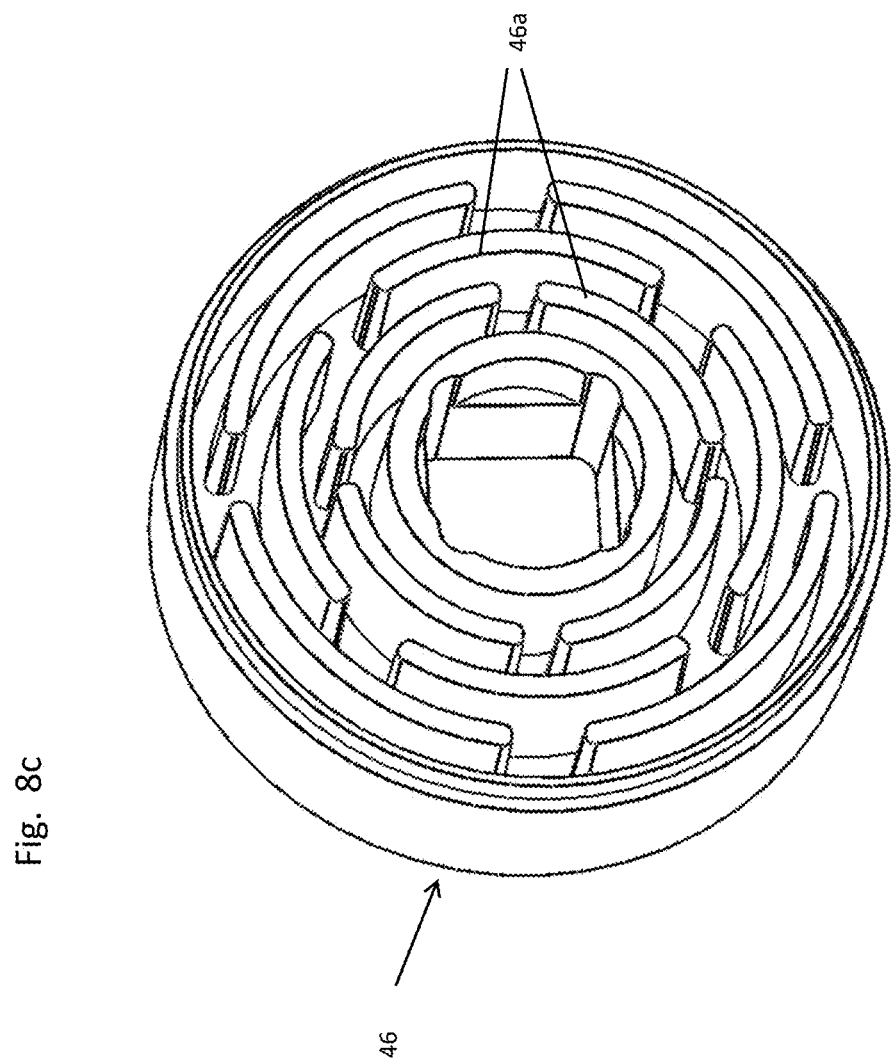
Figure 8D:
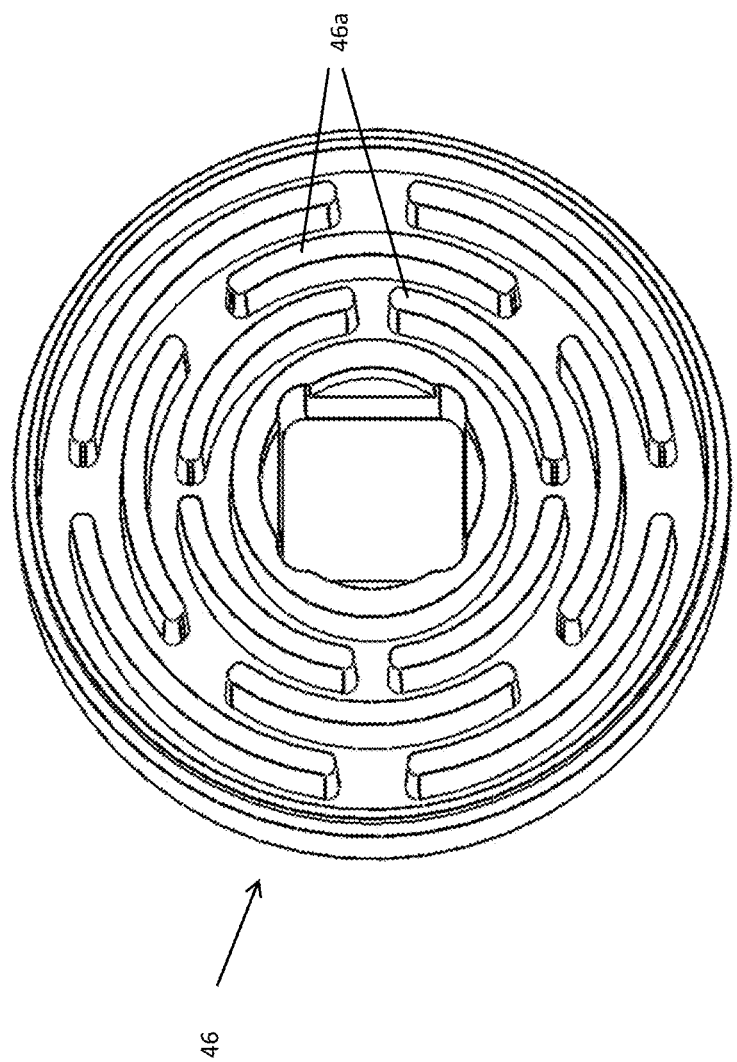
Figure 8E:
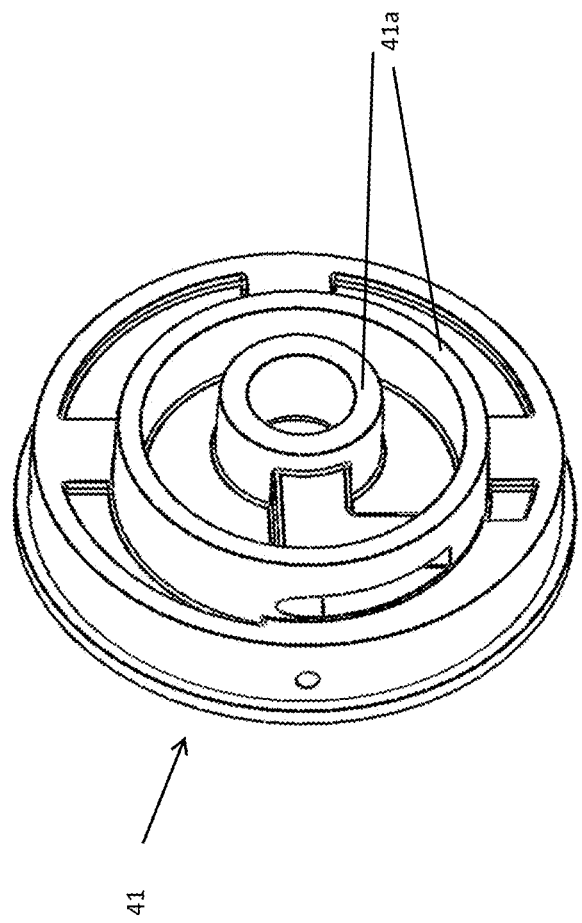
FIG. 8e illustrates a first variation of the embodiment shown in FIG. 8b.
Figure 8F:
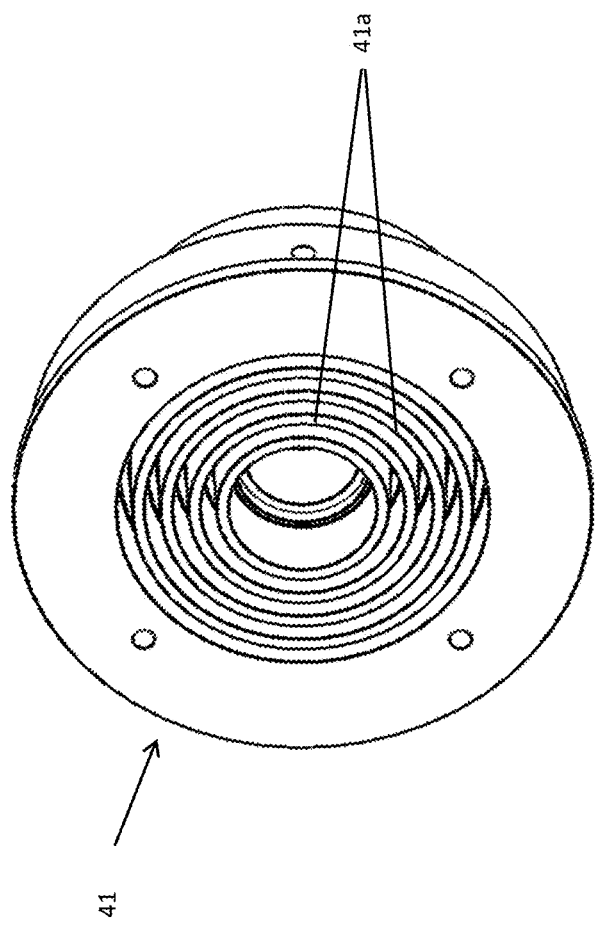
FIG. 8f illustrates a second variation of the embodiment shown in FIG. 8b.
Figure 8G:
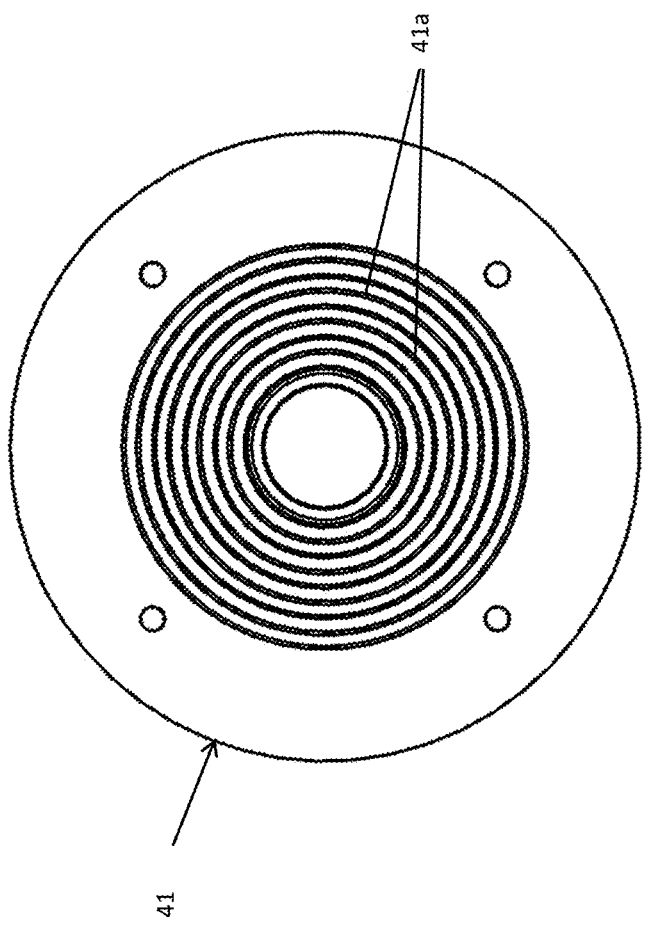
FIG. 8g illustrates a third variation of the embodiment shown in FIG. 8b.

In the variation thereof shown in FIG. 7b, the roller arrangement comprises a single torsion spring 43a The engagement axle flange 46 and the engagement roller flange 41 forming the restraint are shown in more details in FIGS. 8a and 8b, where FIG. 8a show the engagement face of the engagement axle flange 46 facing the engagement roller flange 41 and FIG. 8b show the engagement face of the engagement roller flange 41 facing the engagement axle flange 46.

As shown in FIG. 9, the engagement axle flange 46 is engaged with the engagement roller flange 41 via their respective engagement faces to thereby forming the rotational restraint, restraining the rotation of the roller body to a predefined rotation rate.

The engagement roller flange 41 comprises annular channels 41a and engagement axle flange 46 comprises annular sections of flanges 46a engaged into the annular channels 41a of the engagement roller flange. A lubricate may be located in annular channels 41 as described above, preferably to fill up the major part of the space in the channels 41a between the annular sections of flanges 46a. There by a desired damping of the force transferred from the spring arrangement to the roller body may be ensured.

Figure 9B:
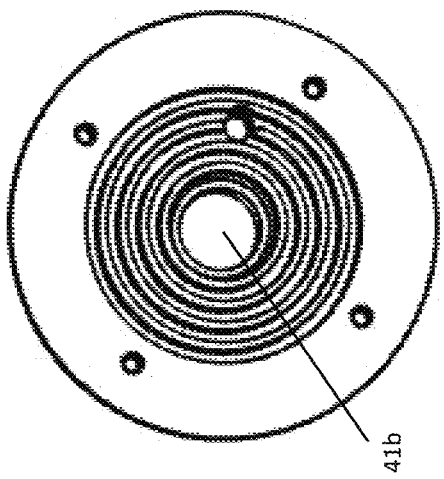
FIGS. 9a and 9b are schematic and perspective views of another set of engagement flanges forming a rotational restraint.
Figure 9A:
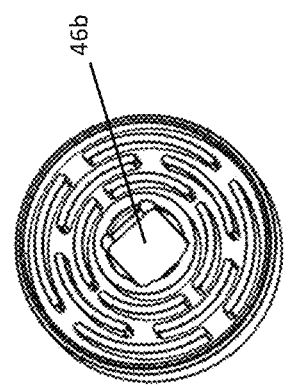

FIGS. 9a and 9b provides another view of the engagement axle flange 46 and the engagement roller flange 41. Here it can be seen that the engagement axle flange 46 has a square center hole, which is fitted to the shape of the axle and thereby rigidly locking the engagement axle flange 46 to the axle. The engagement roller flange 41 has a circular center hole, which ensures that the engagement roller flange 41 is not locked to the axle.

Returning now to FIG. 7. Here it can be seen that the axle has a mounting hole 44a at each end for rigidly mounting the track engagement arrangement, so that when the track engagement arrangement is engaged with the tracks, the axle is prevented from rotate.

Thereby in use, when the torsion springs 43a, 43b are released the springs will 43a, 43b force the roller body to rotate relative to the axle flange 47 which at this stage is locket to the axle via axle flange 45, and thereby the springs will 43a, 43b force the roller body to rotate relative to the axle 44. Since the axle 44 is restricted to rotate by the track engagement arrangements, the roller arrangement will be forced to roll and the mat will be rolled onto the roller body while simultaneously liquid will be dispensed from a compressible bag located onto the mat.

Figure 10:
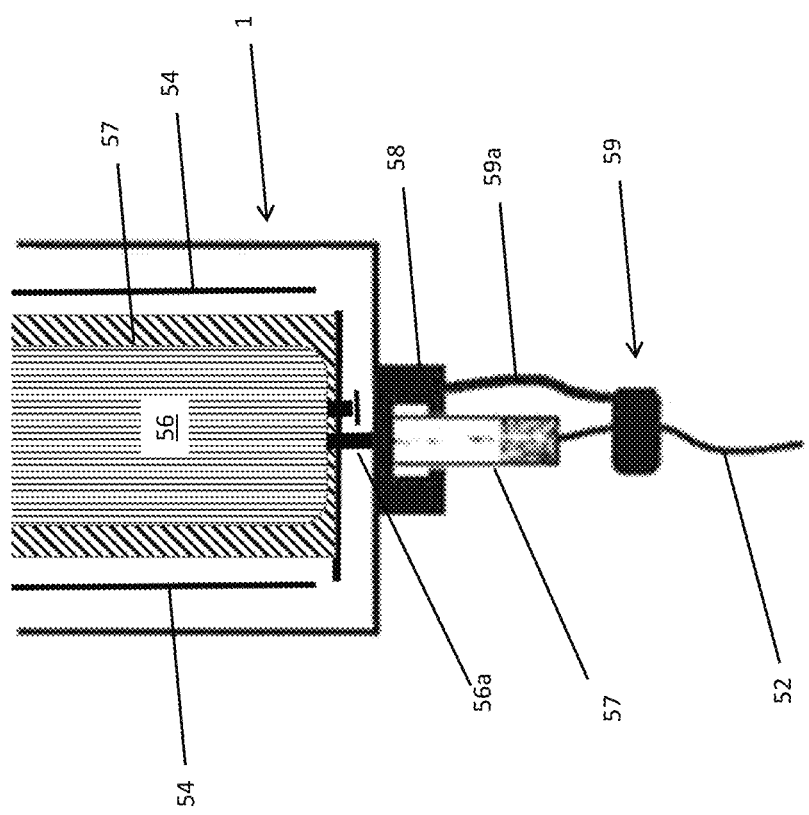
FIG. 10 illustrates an assembly system of an embodiment of the invention comprising a tubing arrangement for administering the liquid comprising a drip chamber a tube and a roller pinch clamp.

FIG. 10 shows a schematic top view of a portion of an apparatus 1 with the mat 57 and steering tracks 54. Onto the mat is located a compressible bag 56 with a liquid for dispensing via a dispensing arrangement 56a, that are arranged to drip into a drip chamber 57. The drip chamber 57 is fixed to the apparatus 1 via a holding arrangement 58. A tube 52 is arranged for transporting the liquid from the drip chamber 57 to a patient. A roller pinch clamp 59 as described above is arranged for adjusting the administration rate. The roller pinch clamp may be fixed to the holding arrangement 58 via an adjustable strap 59a.

The invention claimed is:

1. An assembly suitable for dispensing liquid from a compressible bag, the assembly comprising an apparatus and a flexible mat, the apparatus comprises a housing having a dispensing end and an opposite rear end, a floor comprising a flat floor surface, a pair of parallel guiding tracks and a roller arrangement comprising a roller body having a first and a second roller body ends and a roller surface with a cross-sectional circumference, the roller arrangement has a first roller arrangement end and a second roller arrangement end, respectively engaged with said respective guiding tracks, wherein said guiding tracks are located to guide said roller arrangement to roll said roller arrangement from the rear end location towards the dispensing end, said mat has a length extending between a first mat end and a second mat end, wherein the first mat end is mounted to or adapted to be mounted to said roller body and the mat is located at least partly on the flat floor between said guiding tracks when said roller body is located at said rear end location, wherein said mat has a top surface and an opposite bottom surface facing said floor surface when unrolled from the roller body, wherein said bottom surface has at least one of a lower roughness than said top surface and a coefficient of static friction (CoSF) of 0.3 or less determined according to ASTM D3702-94 (2019).

2. The assembly of claim 1, wherein said mat comprises two or more layers which are interfacially bonded or interconnected at least at the first mat end and the second mat end.

3. The assembly of claim 1, wherein said mounting of the mat to said roller body is a mounting comprising at least one of a chemical mounting, a physical mounting and a mechanical mounting.

4. The assembly claim 1, wherein said mat at the second mat end has a stop arrangement preventing the second end of the mat to be rolled onto the roller body.

5. The assembly claim 4, wherein said roller arrangement comprises a track engagement arrangement at each of the respective first second ends of the roller arrangement engaged with said respective guiding tracks, wherein said stop arrangement comprises a rigid stopper adapted for being blocked by said track engagement arrangements when the track engagement arrangements reached the second end of the mat.

6. The assembly claim 1, wherein said apparatus comprises a drive arrangement engaged with said roller arrangement for driving said roll of the roller arrangement from the rear end towards the dispensing end, said drive arrangement comprises at least one of a spring arrangement and an electric motor.

7. The assembly of claim 6, wherein said drive arrangement comprises a spring arrangement selected from a single spring or a multi spring arrangement and wherein spring arrangement being at least partly located in the roller body.

8. The assembly of claim 7, wherein said spring arrangement comprises a loading arrangement for at least partly loading said spring arrangement wherein said loading arrangement is arranged for at least partly loading said spring arrangement by at least one of unrolling the mat from the roller body and moving the roller arrangement in a direction from the dispensing end and towards the rear end.

9. An assembly suitable for dispensing liquid from a compressible bag, the assembly comprising an apparatus and a flexible mat, the apparatus comprises a housing having a dispensing end and an opposite rear end, a floor comprising a flat floor surface, a pair of parallel guiding tracks and a roller arrangement comprising a roller body having a first and a second roller body ends and a roller surface with a cross-sectional circumference, the roller arrangement has a first roller arrangement end and a second roller arrangement end, respectively engaged with said respective guiding tracks, wherein said guiding tracks are located to guide said roller arrangement to roll said roller arrangement from the rear end location towards the dispensing end, said mat has a length extending between a first mat end and a second mat end, wherein the first mat end is mounted to or adapted to be mounted to said roller body and the mat is located at least partly on the flat floor between said guiding tracks when said roller body is located at said rear end location, wherein said floor surface has a CoSF of 0.4 or less determined according to ASTM D3702-94 (2019).

10. An assembly suitable for dispensing liquid from a compressible bag, the assembly comprising an apparatus and a flexible mat, the apparatus comprises a housing having a dispensing end and an opposite rear end, a floor comprising a flat floor surface, a pair of parallel guiding tracks and a roller arrangement comprising a roller body having a first and a second roller body ends and a roller surface with a cross-sectional circumference, the roller arrangement has a first roller arrangement end and a second roller arrangement end, respectively engaged with said respective guiding tracks, wherein said guiding tracks are located to guide said roller arrangement to roll said roller arrangement from the rear end location towards the dispensing end, said mat has a length extending between a first mat end and a second mat end, wherein the first mat end is mounted to or adapted to be mounted to said roller body and the mat is located at least partly on the flat floor between said guiding tracks when said roller body is located at said rear end location, wherein said roller arrangement comprises a track engagement arrangement at each of the respective first and second ends of the roller arrangement engaged with said respective guiding tracks, wherein at least one of said track engagement arrangements comprises a track slider engaged with said guiding track for sliding along the guiding tracks.

11. The assembly of any one of claim 10, wherein the track engagement arrangements are engaged with said respective guiding tracks to hold the roller body at a predefined or selectable distance to said flat floor surface when the roller arrangement passes from the rear end towards the dispensing end.

12. An assembly suitable for dispensing liquid from a compressible bag, the assembly comprising an apparatus and a flexible mat, the apparatus comprises a housing having a dispensing end and an opposite rear end, a floor comprising a flat floor surface, a pair of parallel guiding tracks and a roller arrangement comprising a roller body having a first and a second roller body ends and a roller surface with a cross-sectional circumference, the roller arrangement has a first roller arrangement end and a second roller arrangement end, respectively engaged with said respective guiding tracks, wherein said guiding tracks are located to guide said roller arrangement to roll said roller arrangement from the rear end location towards the dispensing end, said mat has a length extending between a first mat end and a second mat end, wherein the first mat end is mounted to or adapted to be mounted to said roller body and the mat is located at least partly on the flat floor between said guiding tracks when said roller body is located at said rear end location, wherein said apparatus comprises a drive arrangement engaged with said roller arrangement for driving said roll of the roller arrangement from the rear end towards the dispensing end, said drive arrangement comprises at least one of a spring arrangement and an electric motor, wherein said drive arrangement comprises a spring arrangement selected from a single spring or a multi spring arrangement, wherein said spring arrangement comprises at least one helical torsion spring located within the roller body, wherein said roller arrangement comprises an axle and wherein said roller body is arranged to rotate around said axle.

13. The assembly of claim 12, wherein said spring arrangement is arranged to drive said roller body to rotate around the axle, wherein the axle is rigidly connected to at least one axle flange and wherein a first end of the at least one helical torsion spring is engaged with said roller body and a second end of the at least one helical torsion spring is engaged with said at least one axle flange, wherein the roller body comprises a cylindrical body part and at least one roller flange perpendicular to the cylindrical body and wherein the first end of the at least one helical torsion spring is engaged with said at least one roller flange or said cylindrical body part and wherein said at least one axle flange is an engagement axle flange and said at least one roller flange is an engagement roller flange, wherein said engagement axle flange is engaged with said engagement roller flange.

14. The assembly of claim 13, wherein said engagement axle flange and said engagement roller flange forms a rotational restraint, wherein a first of said engagement axle flange and said engagement roller flange comprises annular channels and a second of said engagement axle flange and said engagement roller flange comprises annular flanges or sections of flanges engaged into the annular channels of said first of said engagement axle flange and said engagement roller flange.

15. The assembly of claim 14, wherein said annular channels comprises a lubricate filling up space in the annular channels between the annular flanges or sections of flanges and wherein said lubricate can pass from one annular channel to another annular channel of the annular channels.

16. An assembly suitable for dispensing liquid from a compressible bag, the assembly comprising an apparatus and a flexible mat,
the apparatus comprises a housing having a dispensing end and an opposite rear end, a floor comprising a flat floor surface, a pair of parallel guiding tracks and a roller arrangement comprising a roller body having a first and a second roller body ends and a roller surface with a cross-sectional circumference, the roller arrangement has a first roller arrangement end and a second roller arrangement end, respectively engaged with said respective guiding tracks, wherein said guiding tracks are located to guide said roller arrangement to roll said roller arrangement from the rear end location towards the dispensing end,
said mat has a length extending between a first mat end and a second mat end, wherein the first mat end is mounted to or adapted to be mounted to said roller body and the mat is located at least partly on the flat floor between said guiding tracks when said roller body is located at said rear end location,
wherein said apparatus comprises a drive arrangement engaged with said roller arrangement for driving said roll of the roller arrangement from the rear end towards the dispensing end, said drive arrangement comprises at least one of a spring arrangement and an electric motor,
wherein said drive arrangement comprises a spring arrangement selected from a single spring or a multi spring arrangement and wherein spring arrangement being at least partly located in the roller body,
wherein said spring arrangement comprises a loading station for loading said spring arrangement, wherein said roller arrangement comprises a snap lock for temporarily holding said roller body in said loading station and wherein said roller arrangement comprises a lever for releasing said roller body from said loading station.

17. An assembly suitable for dispensing liquid from a compressible bag, the assembly comprising an apparatus and a flexible mat,
the apparatus comprises a housing having a dispensing end and an opposite rear end, a floor comprising a flat floor surface, a pair of parallel guiding tracks and a roller arrangement comprising a roller body having a first and a second roller body ends and a roller surface with a cross-sectional circumference, the roller arrangement has a first roller arrangement end and a second roller arrangement end, respectively engaged with said respective guiding tracks, wherein said guiding tracks are located to guide said roller arrangement to roll said roller arrangement from the rear end location towards the dispensing end,
said mat has a length extending between a first mat end and a second mat end, wherein the first mat end is mounted to or adapted to be mounted to said roller body and the mat is located at least partly on the flat floor between said guiding tracks when said roller body is located at said rear end location, wherein the apparatus comprises at least one of
a monitor sensor and a display for monitoring and displaying least one condition of the compressible bag arranged on the mat, wherein the at least one condition being selected from a temperature of the liquid in the bag, and a dispensing condition, and
a regulator arrangement for automatic or remote controlling start or stop of dispensing of the liquid from the compressible bag located on the mat.

18. The assembly of claim 17, wherein the monitor sensor is a temperature regulating arrangement adapted to heat the liquid in the compressible bag located on the mat.

19. The assembly of claim 17, wherein the temperature regulating arrangement comprises one or more heating elements incorporated into at least one of the mat, the floor and a lid, wherein the temperature regulating arrangement comprises an air heat blower arranged for heating a space within the housing to a selected temperature.

20. A system suitable for dispensing liquid from a compressible bag, the system comprising an assembly and the compressible bag, the assembly comprises an apparatus comprising a housing having a dispensing end and an opposite rear end, a floor comprising a flat floor surface, a pair of parallel guiding tracks and a roller arrangement comprising a roller body having a first and a second roller body ends and a roller surface with a cross-sectional circumference, the roller arrangement has a first roller arrangement end and a second roller arrangement end, respectively engaged with said respective guiding tracks, wherein said guiding tracks are located to guide said roller arrangement to roll said roller arrangement from the rear end location towards the dispensing end, and
a mat having a length extending between a first mat end and a second mat end, wherein the first mat end is mounted to or adapted to be mounted to said roller body and the mat is located at least partly on the flat floor between said guiding tracks when said roller body is located at said rear end location,
the compressible bag has a rear end and a dispensing end, the dispensing end comprises a dispensing port suitable for being connected to a tubing arrangement for administering the liquid, wherein a track engagement arrangements are engaged with said respective guiding tracks to hold the roller body at a predefined or selectable distance to said flat floor surface when the roller arrangement passes from the rear end towards the dispensing end, wherein said predefined or selectable distance to said flat floor surface is from about 1 mm to about 2.5 cm larger than a combined thickness of the mat and the compressible bag in empty condition.

21. The system of claim 20, wherein said system further comprises the tubing arrangement for administering the liquid wherein the tubing arrangement comprises a tube and a roller pinch clamp for adjusting a flow through the tube, wherein the roller pinch clamp comprises at least two adjustment rollers located opposite to each other for directly and or indirectly via a support flange pinching the tube between the at least two adjustment rollers.

22. The system of claim 21, wherein said tubing arrangement comprises a spike and drip chamber connected between the dispensing port and the tube.

* * * * *